US011065251B2

(12) United States Patent
Steidl et al.

(10) Patent No.: US 11,065,251 B2
(45) Date of Patent: Jul. 20, 2021

(54) PAK1 INHIBITORS AND USES THEREOF

(71) Applicant: Albert Einstein College of Medicine, Bronx, NY (US)

(72) Inventors: Ulrich Steidl, New Rochelle, NY (US); Ashley M. Eckel, Bothell, WA (US); Robert F. Stanley, New York, NY (US); Boris Rogovoy, San Diego, CA (US); Ilya Okun, San Diego, CA (US)

(73) Assignee: ALBERT EINSTEIN COLLEGE OF MEDICINE, Bronx, NY (US)

( * ) Notice: Subject to any disclaimer, the term of this patent is extended or adjusted under 35 U.S.C. 154(b) by 330 days.

(21) Appl. No.: 16/095,709

(22) PCT Filed: Apr. 3, 2017

(86) PCT No.: PCT/US2017/025673
§ 371 (c)(1),
(2) Date: Oct. 23, 2018

(87) PCT Pub. No.: WO2017/192228
PCT Pub. Date: Nov. 9, 2017

(65) Prior Publication Data
US 2020/0323855 A1 Oct. 15, 2020

Related U.S. Application Data

(60) Provisional application No. 62/332,508, filed on May 6, 2016.

(51) Int. Cl.
*A61K 31/519* (2006.01)
*A61P 35/00* (2006.01)
*A61K 31/437* (2006.01)
*A61K 31/496* (2006.01)
*C07D 471/04* (2006.01)

(52) U.S. Cl.
CPC .......... *A61K 31/519* (2013.01); *A61K 31/437* (2013.01); *A61K 31/496* (2013.01); *A61P 35/00* (2018.01); *C07D 471/04* (2013.01)

(58) Field of Classification Search
CPC .. A61K 31/437; A61K 31/519; A61K 31/496; C07D 47/104; C07D 287/04; C07D 261/08
See application file for complete search history.

(56) References Cited

U.S. PATENT DOCUMENTS

| | | |
|---|---|---|
| 2009/0197862 A1 | 8/2009 | Steinig et al. |
| 2010/0173930 A1 | 7/2010 | Muci et al. |
| 2012/0101122 A1 | 4/2012 | Farkas et al. |
| 2012/0270866 A1 | 10/2012 | Vollrath et al. |
| 2014/0303140 A1 | 10/2014 | Heckmann et al. |
| 2014/0343066 A1 | 11/2014 | Arkitopoulou-Zanze et al. |
| 2015/0359815 A1 | 12/2015 | Steidl et al. |

FOREIGN PATENT DOCUMENTS

| | | | |
|---|---|---|---|
| WO | 2010032195 A1 | | 3/2010 |
| WO | WO 2016201370 | * | 12/2016 |

OTHER PUBLICATIONS

Pandolfi. Blood, 2015, 126 (9), 1118-1127 (Year: 2015).*
Kichina. Expert Opinion on Therapeutic Targets, 2010, 14:7, 703-725 (Year: 2010).*
PCT International Search Report and Written Opinion dated Aug. 16, 2017 for PCT International Patent Application PCT/US2017/025673, 12 pages.
PUBMED-CID 7338118, National Center for Biotechnology Information, Create Date: Jul. 29, 2006, 11 pages.

* cited by examiner

*Primary Examiner* — Noble E Jarrell
(74) *Attorney, Agent, or Firm* — Fox Rothschild LLP

(57) ABSTRACT

Methods are disclosed for treating acute myeloid leukemia (AML) and myelodysplastic syndromes (MDS) using compounds that inhibit p21 protein (Cdc42/Rac)-activated kinase (PAK1).

34 Claims, 18 Drawing Sheets

Specification includes a Sequence Listing.

470 nM                               490 nM
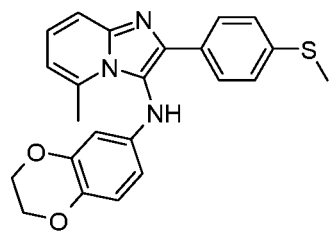 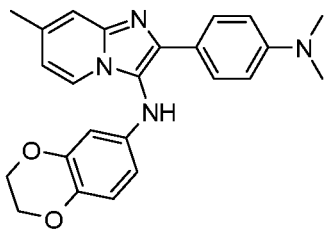
C273-0489                            C273-0466
1-5 µM
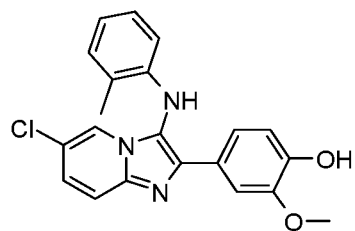 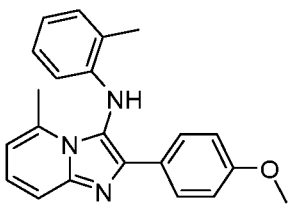
C273-0242                            C273-0249
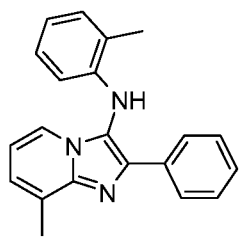 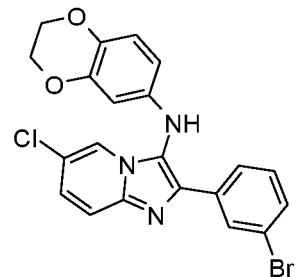
C273-0257                            C273-0500
FIG. 2

| DiscoveRx Gene Symbol | Entrez Gene Symbol | C273-0489 | DiscoveRx Symbol | Entrez Gene Symbol | C273-0489 | DiscoveRx Gene Symbol | Entrez Gene Symbol | C273-0489 |
|---|---|---|---|---|---|---|---|---|
| ABL1(E255K)-phosphorylated | ABL1 | 73 | ERBB4 | ERBB4 | 100 | PCTK1 | CDK16 | 99 |
| ABL1(T315I)-phosphorylated | ABL1 | 92 | ERK1 | MAPK3 | 100 | PDGFRA | PDGFRA | 100 |
| ABL1-non-phosphorylated | ABL1 | 100 | FAK | PTK2 | 93 | PDGFRB | PDGFRB | 95 |
| ABL1-phosphorylated | ABL1 | 90 | FGFR2 | FGFR2 | 94 | PDPK1 | PDPK1 | 100 |
| ACVR1B | ACVR1B | 100 | FGFR3 | FGFR3 | 100 | PIK3C2B | PIK3C2B | 90 |
| ADCK3 | CABC1 | 100 | FLT3 | FLT3 | 87 | PIK3CA | PIK3CA | 95 |
| AKT1 | AKT1 | 99 | GSK3B | GSK3B | 86 | PIK3CG | PIK3CG | 100 |
| AKT2 | AKT2 | 69 | IGF1R | IGF1R | 98 | PIM1 | PIM1 | 100 |
| ALK | ALK | 100 | IKK-alpha | CHUK | 100 | PIM2 | PIM2 | 100 |
| AURKA | AURKA | 90 | IKK-beta | IKBKB | 100 | PIM3 | PIM3 | 98 |
| AURKB | AURKB | 96 | INSR | INSR | 99 | PKAC-alpha | PRKACA | 96 |
| AXL | AXL | 95 | JAK2(JH1domain-catalytic) | JAK2 | 89 | PLK1 | PLK1 | 100 |
| BMPR2 | BMPR2 | 97 | JAK3(JH1domain-catalytic) | JAK3 | 100 | PLK3 | PLK3 | 94 |
| BRAF | BRAF | 97 | JNK1 | MAPK8 | 100 | PLK4 | PLK4 | 100 |
| BRAF V600E | BRAF | 90 | JNK2 | MAPK9 | 93 | PRKCE | PRKCE | 100 |
| BTK | BTK | 85 | JNK3 | MAPK10 | 100 | RAF1 | RAF1 | 100 |
| CDK11 | CDK19 | 87 | KIT | KIT | 99 | RET | RET | 91 |
| CDK2 | CDK2 | 92 | KIT(D816V) | KIT | 93 | RIOK2 | RIOK2 | 100 |

FIG. 3A

| DiscoveRx Gene Symbol | Entrez Gene Symbol | C273-0489 | DiscoveRx Symbol | Entrez Gene Symbol | C273-0489 | DiscoveRx Gene Symbol | Entrez Gene Symbol | C273-0489 |
|---|---|---|---|---|---|---|---|---|
| CDK3 | CDK3 | 95 | KIT V559D,T670I | KIT | 95 | ROCK2 | ROCK2 | 99 |
| CDK7 | CDK7 | 69 | LKB1 | STK11 | 100 | RSK2(Kin.Dom.1-N-terminal) | RPS6KA3 | 97 |
| CDK9 | CDK9 | 97 | MAP3K4 | MAP3K4 | 93 | SNARK | NUAK2 | 98 |
| CHEK1 | CHEK1 | 93 | MAPKAPK2 | MAPKAPK2 | 100 | SRC | SRC | 99 |
| CSF1R | CSF1R | 92 | MARK3 | MARK3 | 93 | SRPK3 | SRPK3 | 99 |
| CSNK1D | CSNK1D | 95 | MEK1 | MAP2K1 | 100 | TGFBR1 | TGFBR1 | 97 |
| CSNK1G2 | CSNK1G2 | 97 | MEK2 | MAP2K2 | 100 | TIE2 | TEK | 100 |
| DCAMKL1 | DCLK1 | 97 | MET | MET | 100 | TRKA | NTRK1 | 86 |
| DYRK1B | DYRK1B | 96 | MKNK1 | MKNK1 | 100 | TSSK1B | TSSK1B | 62 |
| EGFR | EGFR | 97 | MKNK2 | MKNK2 | 86 | TYK2(JH1domain-catalytic) | TYK2 | 89 |
| EGFR L858R | EGFR | 91 | MLK1 | MAP3K9 | 100 | ULK2 | ULK2 | 100 |
| EPHA2 | EPHA2 | 100 | p38-alpha | MAPK14 | 100 | VEGFR2 | KDR | 94 |
| ERBB2 | ERBB2 | 100 | p38-beta | MAPK11 | 100 | YANK3 | STK32C | 63 |
| | | | | | | ZAP70 | ZAP70 | 100 |

FIG. 3B

| PO plasma | | IV plasma | | Fabs, % |
|---|---|---|---|---|
| AUClast | Dose, mg/ | AUClast | Dose, mg/kg | |
| 92.7 | 10 | 129 | 2 | 14.4% |
| AUCINF | Dose, mg/ | AUCINF | Dose, mg/kg | |
| | 10 | | 2 | #DIV/0! |

| DiscoveRx Gene Symbol | Entrez Gene Symbol | T813 0242 | DiscoveRx Gene Symbol | Entrez Gene Symbol | T813-0242 | DiscoveRx Gene Symbol | Entrez Gene Symbol | T813 0242 |
|---|---|---|---|---|---|---|---|---|
| ABL1(E255K)-phosphorylated | ABL1 | 70 | ERBB4 | ERBB4 | 97 | PCTK1 | CDK16 | 95 |
| ABL1(T315I)-phosphorylated | ABL1 | 83 | ERK1 | MAPK3 | 100 | PDGFRA | PDGFRA | 83 |
| ABL1-non-phosphorylated | ABL1 | 99 | FAK | PTK2 | 100 | PDGFRB | PDGFRB | 83 |
| ABL1-phosphorylated | ABL1 | 89 | FGFR2 | FGFR2 | 80 | PDPK1 | PDPK1 | 100 |
| ACVR1B | ACVR1B | 91 | FGFR3 | FGFR3 | 100 | PIK3C2B | PIK3C2B | 89 |
| ADCK3 | CABC1 | 100 | FLT3 | FLT3 | 100 | PIK3CA | PIK3CA | 89 |
| AKT1 | AKT1 | 90 | GSK3B | GSK3B | 79 | PIK3CG | PIK3CG | 100 |
| AKT2 | AKT2 | 89 | IGF1R | IGF1R | 100 | PIM1 | PIM1 | 93 |
| ALK | ALK | 90 | IKK-alpha | CHUK | 96 | PIM2 | PIM2 | 100 |
| AURKA | AURKA | 70 | IKK-beta | IKBKB | 100 | PIM3 | PIM3 | 99 |
| AURKB | AURKB | 91 | INSR | INSR | 96 | PKAC-alpha | PRKACA | 93 |
| AXL | AXL | 100 | JAK2(JH1domain-catalytic) | JAK2 | 72 | PLK1 | PLK1 | 96 |
| BMPR2 | BMPR2 | 91 | JAK3(JH1domain-catalytic) | JAK3 | 99 | PLK3 | PLK3 | 83 |
| BRAF | BRAF | 100 | JNK1 | MAPK8 | 95 | PLK4 | PLK4 | 100 |
| BRAF V600E | BRAF | 92 | JNK2 | MAPK9 | 80 | PRKCE | PRKCE | 99 |
| BTK | BTK | 81 | JNK3 | MAPK10 | 92 | RAF1 | RAF1 | 99 |

FIG. 6A

| DiscoveRx Gene Symbol | Entrez Gene Symbol | T813 0242 | DiscoveRx Gene Symbol | Entrez Gene Symbol | T813-0242 | DiscoveRx Gene Symbol | Entrez Gene Symbol | T813 0242 |
|---|---|---|---|---|---|---|---|---|
| CDK11 | CDK19 | 100 | KIT | KIT | 96 | RET | RET | 99 |
| CDK2 | CDK2 | 96 | KIT(D816V) | KIT | 90 | RIOK2 | RIOK2 | 93 |
| CDK3 | CDK3 | 94 | KIT(V559D,T670I) | KIT | 97 | ROCK2 | ROCK2 | 77 |
| CDK7 | CDK7 | 84 | LKB1 | STK11 | 100 | RSK2(Kin.Dom-1-N-terminal) | RPS6KA3 | 87 |
| CDK9 | CDK9 | 88 | MAP3K4 | MAP3K4 | 78 | SNARK | NUAK2 | 72 |
| CHEK1 | CHEK1 | 100 | MAPKAPK2 | MAPKAPK2 | 100 | SRC | SRC | 98 |
| CSF1R | CSF1R | 91 | MARK3 | MARK3 | 100 | SRPK3 | SRPK3 | 99 |
| CSNK1D | CSNK1D | 98 | MEK1 | MAP2K1 | 88 | TGFBR1 | TGFBR1 | 92 |
| CSNK1G2 | CSNK1G2 | 100 | MEK2 | MAP2K2 | 89 | TIE2 | TEK | 88 |
| DCAMKL1 | DCLK1 | 70 | MET | MET | 100 | TRKA | NTRK1 | 83 |
| DYRK1B | DYRK1B | 93 | MKNK1 | MKNK1 | 98 | TSSK1B | TSSK1B | 100 |
| EGFR | EGFR | 100 | MKNK2 | MKNK2 | 80 | TYK2 (JH1domain-catalytic) | TYK2 | 61 |
| EGFR L858R | EGFR | 100 | MLK1 | MAP3K9 | 100 | ULK2 | ULK2 | 92 |
| EPHA2 | EPHA2 | 99 | p38-alpha | MAPK14 | 94 | VEGFR2 | KDR | 83 |
| ERBB2 | ERBB2 | 92 | p38-beta | MAPK11 | 91 | YANK3 | STK32C | 83 |
| | | | | | | ZAP70 | ZAP70 | 98 |

FIG. 6B

| DiscoveRx Gene Symbol | Entrez Gene Symbol | D245-0091 | DiscoveRx Symbol | Entrez Gene Symbol | D245-0091 | DiscoveRx Gene Symbol | Entrez Gene Symbol | D245-0091 |
|---|---|---|---|---|---|---|---|---|
| ABL1(E255K) phosphorylated | ABL1 | 68 | ERBB4 | ERBB4 | 100 | PCTK1 | CDK16 | 92 |
| ABL1(T315I)-phosphorylated | ABL1 | 73 | ERK1 | MAPK3 | 89 | PDGFRA | PDGFRA | 94 |
| ABL1-non-phosphorylated | ABL1 | 83 | FAK | PTK2 | 89 | PDGFRB | PDGFRB | 88 |
| ABL1-phosphorylated | ABL1 | 75 | FGFR2 | FGFR2 | 72 | PDPK1 | PDPK1 | 97 |
| ACVR1B | ACVR1B | 89 | FGFR3 | FGFR3 | 97 | PIK3C2B | PIK3C2B | 91 |
| ADCK3 | CABC1 | 100 | FLT3 | FLT3 | 96 | PIK3CA | PIK3CA | 91 |
| AKT1 | AKT1 | 87 | GSK3B | GSK3B | 87 | PIK3CG | PIK3CG | 100 |
| AKT2 | AKT2 | 97 | IGF1R | IGF1R | 92 | PIM1 | PIM1 | 93 |
| ALK | ALK | 90 | IKK-alpha | CHUK | 95 | PIM2 | PIM2 | 90 |
| AURKA | AURKA | 74 | IKK-beta | IKBKB | 100 | PIM3 | PIM3 | 85 |
| AURKB | AURKB | 90 | INSR | INSR | 98 | PKAC-alpha | PRKACA | 82 |
| AXL | AXL | 88 | JAK2(JH1domain-catalytic) | JAK2 | 83 | PLK1 | PLK1 | 91 |
| BMPR2 | BMPR2 | 86 | JAK3(JH1domain-catalytic) | JAK3 | 99 | PLK3 | PLK3 | 94 |
| BRAF | BRAF | 98 | JNK1 | MAPK8 | 81 | PLK4 | PLK4 | 100 |
| BRAF V600E | BRAF | 87 | JNK2 | MAPK9 | 72 | PRKCE | PRKCE | 98 |
| BTK | BTK | 90 | JNK3 | MAPK10 | 85 | RAF1 | RAF1 | 96 |
| CDK11 | CDK19 | 100 | KIT | KIT | 88 | RET | RET | 89 |
| CDK2 | CDK2 | 85 | KIT(D816V) | KIT | 83 | RIOK2 | RIOK2 | 94 |

FIG. 9A

| DiscoveRx Gene Symbol | Entrez Gene Symbol | D245-0091 | DiscoveRx Symbol | Entrez Gene Symbol | D245-0091 | DiscoveRx Symbol | Entrez Gene Symbol | D245-0091 |
|---|---|---|---|---|---|---|---|---|
| CDK3 | CDK3 | 94 | KIT V559D,T670I | KIT | 96 | ROCK2 | ROCK2 | 72 |
| CDK7 | CDK7 | 75 | LKB1 | STK11 | 100 | RSK2(Kin.Dom.1-N-terminal) | RPS6KA3 | 87 |
| CDK9 | CDK9 | 100 | MAP3K4 | MAP3K4 | 71 | SNARK | NUAK2 | 84 |
| CHEK1 | CHEK1 | 93 | MAPKAPK2 | MAPKAPK2 | 100 | SRC | SRC | 85 |
| CSF1R | CSF1R | 94 | MARK3 | MARK3 | 99 | SRPK3 | SRPK3 | 97 |
| CSNK1D | CSNK1D | 94 | MEK1 | MAP2K1 | 93 | TGFBR1 | TGFBR1 | 99 |
| CSNK1G2 | CSNK1G2 | 88 | MEK2 | MAP2K2 | 79 | TIE2 | TEK | 93 |
| DCAMKL1 | DCLK1 | 79 | MET | MET | 89 | TRKA | NTRK1 | 78 |
| DYRK1B | DYRK1B | 100 | MKNK1 | MKNK1 | 100 | TSSK1B | TSSK1B | 93 |
| EGFR | EGFR | 77 | MKNK2 | MKNK2 | 91 | TYK2(JH1domain-catalytic) | TYK2 | 75 |
| EGFR L858R | EGFR | 80 | MLK1 | MAP3K9 | 94 | ULK2 | ULK2 | 85 |
| EPHA2 | EPHA2 | 93 | p38-alpha | MAPK14 | 84 | VEGFR2 | KDR | 85 |
| ERBB2 | ERBB2 | 99 | p38-beta | MAPK11 | 96 | YANK3 | STK32C | 81 |
| | | | | | | ZAP70 | ZAP70 | 100 |

SEQUENCE LISTING

<160> NUMBER OF SEQ ID NOS: 3

<210> SEQ ID NO 1
<211> LENGTH: 2308
<212> TYPE: DNA
<213> ORGANISM: Homo sapiens

<400> SEQUENCE: 1

| | | | | | |
|---|---|---|---|---|---:|
| aaaactttgg | gagtttttag | agacgagttt | tttttttttt | ctattacttt | tcccccccc | 60 |
| taactaacgg | actattattg | ttgttgtttt | aaatttagct | cttagggctt | agctatttgg | 120 |
| gttttcttgc | ggtgtccggc | tcccgtctcc | ctggctcccc | cgcccgccct | gcggcccag | 180 |
| cgcccctcgc | tctcatccag | cccgcgagga | gtgcgggcgc | cgcgccgcct | ttaaagcgag | 240 |
| gccagggagc | gaggcggtga | ccggccgaga | tccggccctc | gcctcctccc | tcggtggcgc | 300 |
| tagggctccc | ggcctctctt | cctcagtgcg | ggcggagaag | cgaaagcgga | tcgtcctcgg | 360 |
| ctgccgccgc | cttctccggg | actcgcgcgc | ccctccccgc | gcgcccaccc | acccagtccg | 420 |
| gctggactgc | ggcagccgcg | cggctcaccc | cggcaggatg | ttcgcagccg | ggctggctcc | 480 |
| cttctacgcc | tccaacttca | gcctctggtc | ggccgcttac | tgctcctcgg | ccggcccagg | 540 |
| cggctgctcc | ttcccttgg | accccgccgc | cgtcaaaaag | ccctccttct | gcatcgcaga | 600 |
| cattctgcac | gccggcgtgg | gggatctggg | ggcggcccg | gagggcctgg | caggggcctc | 660 |
| ggccgccgcc | ctcaccgcgc | acttgggctc | ggttcacccg | cacgcctctt | ccaagcggc | 720 |
| ggccagatcc | ccgcttcgac | ccaccccagt | ggtggcgccc | tccgaagtcc | cggctggctt | 780 |
| cccgcagcgg | ctgtctccgc | tctcagccgc | ctaccaccac | catcacccgc | aacaacaaca | 840 |
| gcagcagcaa | cagccgcagc | agcaacagcc | tccgcctccg | ccccgggctg | gcgccctgca | 900 |
| gccccggcc | tcggggacgc | gagtggttcc | gaacccccac | cacagtggct | ctgccccggc | 960 |
| cccctccagc | aaagacctca | aatttggaat | tgaccgcatt | ttatctgcag | aatttgaccc | 1020 |
| aaaagtcaaa | gaaggcaaca | cgctgagaga | tctcacttcc | ctgctaaccg | gtgggcggcc | 1080 |
| cgccggggtg | cacctctcag | gcctgcagcc | ctcggccggc | cagttcttcg | catctctaga | 1140 |
| tcccattaac | gaggcttctg | caatcctgag | tcccttaaac | tcgaacccaa | gaaattcagt | 1200 |
| tcagcatcag | ttccaagaca | cgtttccagg | tccctatgct | gtgctcacga | aggacaccat | 1260 |
| gccgcagacg | tacaaaagga | agcgttcatg | gtcgcgcgct | gtgttctcca | acctgcagag | 1320 |
| gaaaggcctg | gagaaaaggt | ttgagattca | gaagtacgtg | accaagccgg | accgaaagca | 1380 |
| gctggcggcg | atgctgggcc | tcacggacgc | acaggtgaag | gtgtggttcc | agaaccggcg | 1440 |
| gatgaagtgg | cggcactcca | aggaggccca | ggcccaaaag | gacaaggaca | aggaggctgg | 1500 |
| cgagaagcca | tcaggtggag | ccccggctgc | ggatggcgag | caggacgaga | ggagcccag | 1560 |
| ccgttctgaa | ggcgaggctg | agagcgagag | cagcgactcc | gagtccctgg | acatggcccc | 1620 |
| cagcgacacg | gagcggactg | aggggagtga | gcgttctctg | caccaaacaa | cagttattaa | 1680 |
| ggccccggtc | actggcgccc | tcattaccgc | cagcagtgct | gggagtggtg | ggagcagcgg | 1740 |
| cggcggcggc | aatagtttca | gcttcagcag | cgccagcagt | cttagtagca | gcagcaccag | 1800 |
| tgcgggttgc | gccagcagcc | ttggcggcg | cggcgcctcg | gagcttctcc | ctgcaacaca | 1860 |
| gcccacagcc | agcagcgctc | ccaaaagccc | cgagccagcc | caaggcgcgc | ttggctgctt | 1920 |
| atagactgta | ctagggcgga | ggggatccgg | gccttgcgtg | cagcctccca | accatgggct | 1980 |
| gggttttgtg | cttactgtat | gttggcgact | tggtagggca | ggagacgcag | cgtgagcct | 2040 |
| acctcccgac | attcacgctt | cgccccacgc | tgctccgact | ggctgcagcg | gacactgccc | 2100 |

-continued

```
aaagcagagg ggagtctcag tgtcctgcta gccagccgaa cacttctctc cggaagcagg    2160
ctggttcgac tgtgaggtgt ttgactaaac tgtttctctg actcgcccca gaggtcgtgg    2220
ctcaaaggca cttaggacgc cttaaatttg taaataaaat gtttactacg gtttgtaaaa    2280
aaaaaaaaaa aaaaaaaaaa aaaaaaaa                                       2308

<210> SEQ ID NO 2
<211> LENGTH: 488
<212> TYPE: PRT
<213> ORGANISM: Homo sapiens

<400> SEQUENCE: 2

Met Phe Ala Ala Gly Leu Ala Pro Phe Tyr Ala Ser Asn Phe Ser Leu
1               5                   10                  15

Trp Ser Ala Ala Tyr Cys Ser Ser Ala Gly Pro Gly Gly Cys Ser Phe
            20                  25                  30

Pro Leu Asp Pro Ala Ala Val Lys Lys Pro Ser Phe Cys Ile Ala Asp
        35                  40                  45

Ile Leu His Ala Gly Val Gly Asp Leu Gly Ala Ala Pro Glu Gly Leu
    50                  55                  60

Ala Gly Ala Ser Ala Ala Ala Leu Thr Ala His Leu Gly Ser Val His
65                  70                  75                  80

Pro His Ala Ser Phe Gln Ala Ala Arg Ser Pro Leu Arg Pro Thr
                85                  90                  95

Pro Val Val Ala Pro Ser Glu Val Pro Ala Gly Phe Pro Gln Arg Leu
            100                 105                 110

Ser Pro Leu Ser Ala Ala Tyr His His His Pro Gln Gln Gln Gln
        115                 120                 125

Gln Gln Gln Gln Pro Gln Gln Gln Pro Pro Pro Pro Arg Ala
    130                 135                 140

Gly Ala Leu Gln Pro Pro Ala Ser Gly Thr Arg Val Val Pro Asn Pro
145                 150                 155                 160

His His Ser Gly Ser Ala Pro Ala Pro Ser Ser Lys Asp Leu Lys Phe
                165                 170                 175

Gly Ile Asp Arg Ile Leu Ser Ala Glu Phe Asp Pro Lys Val Lys Glu
            180                 185                 190

Gly Asn Thr Leu Arg Asp Leu Thr Ser Leu Leu Thr Gly Gly Arg Pro
        195                 200                 205

Ala Gly Val His Leu Ser Gly Leu Gln Pro Ser Ala Gly Gln Phe Phe
    210                 215                 220

Ala Ser Leu Asp Pro Ile Asn Glu Ala Ser Ala Ile Leu Ser Pro Leu
225                 230                 235                 240

Asn Ser Asn Pro Arg Asn Ser Val Gln His Gln Phe Gln Asp Thr Phe
                245                 250                 255

Pro Gly Pro Tyr Ala Val Leu Thr Lys Asp Thr Met Pro Gln Thr Tyr
            260                 265                 270

Lys Arg Lys Arg Ser Trp Ser Arg Ala Val Phe Ser Asn Leu Gln Arg
        275                 280                 285

Lys Gly Leu Glu Lys Arg Phe Glu Ile Gln Lys Tyr Val Thr Lys Pro
    290                 295                 300

Asp Arg Lys Gln Leu Ala Ala Met Leu Gly Leu Thr Asp Ala Gln Val
305                 310                 315                 320

Lys Val Trp Phe Gln Asn Arg Arg Met Lys Trp Arg His Ser Lys Glu
                325                 330                 335
```

```
Ala Gln Ala Gln Lys Asp Lys Asp Lys Glu Ala Gly Glu Lys Pro Ser
            340                 345                 350

Gly Gly Ala Pro Ala Ala Asp Gly Glu Gln Asp Glu Arg Ser Pro Ser
            355                 360                 365

Arg Ser Glu Gly Glu Ala Glu Ser Glu Ser Ser Asp Ser Glu Ser Leu
        370                 375                 380

Asp Met Ala Pro Ser Asp Thr Glu Arg Thr Glu Gly Ser Glu Arg Ser
385                 390                 395                 400

Leu His Gln Thr Thr Val Ile Lys Ala Pro Val Thr Gly Ala Leu Ile
                405                 410                 415

Thr Ala Ser Ser Ala Gly Ser Gly Gly Ser Ser Gly Gly Gly Gly Asn
            420                 425                 430

Ser Phe Ser Phe Ser Ser Ala Ser Ser Leu Ser Ser Ser Ser Thr Ser
            435                 440                 445

Ala Gly Cys Ala Ser Ser Leu Gly Gly Gly Ala Ser Glu Leu Leu
        450                 455                 460

Pro Ala Thr Gln Pro Thr Ala Ser Ser Ala Pro Lys Ser Pro Glu Pro
465                 470                 475                 480

Ala Gln Gly Ala Leu Gly Cys Leu
                485

<210> SEQ ID NO 3
<211> LENGTH: 545
<212> TYPE: PRT
<213> ORGANISM: Homo sapiens

<400> SEQUENCE: 3

Met Ser Asn Asn Gly Leu Asp Ile Gln Asp Lys Pro Pro Ala Pro Pro
1               5                   10                  15

Met Arg Asn Thr Ser Thr Met Ile Gly Ala Gly Ser Lys Asp Ala Gly
            20                  25                  30

Thr Leu Asn His Gly Ser Lys Pro Leu Pro Pro Asn Pro Glu Glu Lys
        35                  40                  45

Lys Lys Lys Asp Arg Phe Tyr Arg Ser Ile Leu Pro Gly Asp Lys Thr
    50                  55                  60

Asn Lys Lys Lys Glu Lys Glu Arg Pro Glu Ile Ser Leu Pro Ser Asp
65                  70                  75                  80

Phe Glu His Thr Ile His Val Gly Phe Asp Ala Val Thr Gly Glu Phe
                85                  90                  95

Thr Gly Met Pro Glu Gln Trp Ala Arg Leu Leu Gln Thr Ser Asn Ile
            100                 105                 110

Thr Lys Ser Glu Gln Lys Lys Asn Pro Gln Ala Val Leu Asp Val Leu
        115                 120                 125

Glu Phe Tyr Asn Ser Lys Lys Thr Ser Asn Ser Gln Lys Tyr Met Ser
    130                 135                 140

Phe Thr Asp Lys Ser Ala Glu Asp Tyr Asn Ser Ser Asn Ala Leu Asn
145                 150                 155                 160

Val Lys Ala Val Ser Glu Thr Pro Ala Val Pro Pro Val Ser Glu Asp
                165                 170                 175

Glu Asp Asp Asp Asp Asp Ala Thr Pro Pro Val Ile Ala Pro
            180                 185                 190

Arg Pro Glu His Thr Lys Ser Val Tyr Thr Arg Ser Val Ile Glu Pro
        195                 200                 205

Leu Pro Val Thr Pro Thr Arg Asp Val Ala Thr Ser Pro Ile Ser Pro
```

```
            210                 215                 220
Thr Glu Asn Asn Thr Thr Pro Pro Asp Ala Leu Thr Arg Asn Thr Glu
225                 230                 235                 240

Lys Gln Lys Lys Lys Pro Lys Met Ser Asp Glu Ile Leu Glu Lys
                245                 250                 255

Leu Arg Ser Ile Val Ser Val Gly Asp Pro Lys Lys Tyr Thr Arg
                260                 265                 270

Phe Glu Lys Ile Gly Gln Gly Ala Ser Gly Thr Val Tyr Thr Ala Met
                275                 280                 285

Asp Val Ala Thr Gly Gln Glu Val Ala Ile Lys Gln Met Asn Leu Gln
290                 295                 300

Gln Gln Pro Lys Lys Glu Leu Ile Ile Asn Glu Ile Leu Val Met Arg
305                 310                 315                 320

Glu Asn Lys Asn Pro Asn Ile Val Asn Tyr Leu Asp Ser Tyr Leu Val
                325                 330                 335

Gly Asp Glu Leu Trp Val Val Met Glu Tyr Leu Ala Gly Gly Ser Leu
                340                 345                 350

Thr Asp Val Val Thr Glu Thr Cys Met Asp Glu Gly Gln Ile Ala Ala
                355                 360                 365

Val Cys Arg Glu Cys Leu Gln Ala Leu Glu Phe Leu His Ser Asn Gln
370                 375                 380

Val Ile His Arg Asp Ile Lys Ser Asp Asn Ile Leu Leu Gly Met Asp
385                 390                 395                 400

Gly Ser Val Lys Leu Thr Asp Phe Gly Phe Cys Ala Gln Ile Thr Pro
                405                 410                 415

Glu Gln Ser Lys Arg Ser Thr Met Val Gly Thr Pro Tyr Trp Met Ala
                420                 425                 430

Pro Glu Val Val Thr Arg Lys Ala Tyr Gly Pro Lys Val Asp Ile Trp
                435                 440                 445

Ser Leu Gly Ile Met Ala Ile Glu Met Ile Glu Gly Glu Pro Pro Tyr
                450                 455                 460

Leu Asn Glu Asn Pro Leu Arg Ala Leu Tyr Leu Ile Ala Thr Asn Gly
465                 470                 475                 480

Thr Pro Glu Leu Gln Asn Pro Glu Lys Leu Ser Ala Ile Phe Arg Asp
                485                 490                 495

Phe Leu Asn Arg Cys Leu Glu Met Asp Val Glu Lys Arg Gly Ser Ala
                500                 505                 510

Lys Glu Leu Leu Gln His Gln Phe Leu Lys Ile Ala Lys Pro Leu Ser
                515                 520                 525

Ser Leu Thr Pro Leu Ile Ala Ala Ala Lys Glu Ala Thr Lys Asn Asn
                530                 535                 540

His
545
```

PAK1 INHIBITORS AND USES THEREOF

CROSS-REFERENCE TO RELATED APPLICATIONS

This application is a U.S. national stage entry under 35 U.S.C. § 371 of PCT International Patent Application No. PCT/US2017/025673, filed Apr. 3, 2017, which claims the benefit of U.S. Provisional Patent Application No. 62/332,508, filed May 6, 2016, the contents of each of which are incorporated herein by reference into the subject application.

BACKGROUND OF THE INVENTION

Throughout this application various publications are referred to in parentheses. Full citations for these references may be found at the end of the specification. The disclosures of these publications, and of all patents, patent application publications and books referred to herein, are hereby incorporated by reference in their entirety into the subject application to more fully describe the art to which the subject invention pertains.

Acute myeloid leukemia (AML) and myelodysplastic syndromes (MDS) are heterogeneous clonal neoplastic diseases that originate from transformed cells that have progressively acquired critical genetic changes that disrupt key differentiation- and growth-regulatory pathways (Hanahan and Weinberg, 2000; Marcucci et al., 2011). Less than one third of AML patients achieve durable remission with current treatment regimens, and prognostication and risk stratification of individual patients remains very challenging, in particular in favorable and standard risk groups.

Analysis of pre-leukemic hematopoietic stem and progenitor cells (HSPC) in a murine model of AML revealed the non-clustered H2.0-like homeobox (Hlx) gene to be 4-fold unregulated compared to wild-type (WT) HSPC (Steidl et al., 2006) suggesting that Hlx may be involved in malignant transformation. HLX is the highly conserved human/murine homologue of the homeobox gene H2.0, which shows tissue-specific expression throughout development in Drosophila melanogaster (Allen et al, 1991; Hentsch et al., 1996). Additional studies two decades ago detected HLX expression in hematopoietic progenitors and in leukemic blasts of patients with AML, and a study of HLX-deficient fetal liver cells suggested a decrease of colony-formation capacity (Deguchi and Kehrl, 1991; Deguchi et al., 1992).

Inhibition of p21 protein (Cdc42/Rac)-activated kinase (PAK1) for treatment of AML and MDS has been described (U.S. Patent Application Publication Nos. 2015/0299336 A1 and 2015/0359815 A1). The present invention addresses the need for small molecule treatments for AML and MDS as well as for tumors expressing elevated levels of HLX.

SUMMARY OF THE INVENTION

The invention provides methods of treating acute myeloid leukemia (AML), myelodysplastic syndrome (MDS), or a tumor having elevated expression of H2.0-like homeobox (HLX) and/or elevated expression of p21 protein (Cdc42/Rac)-activated kinase (PAK1) in a subject, the methods comprising administering to the subject a compound of Formula I, II, III or IV, as disclosed herein, in an amount effective to inhibit PAK1 in a subject.

The invention also provides methods of inhibiting PAK1 in a subject, the methods comprising administering to the subject a compound of Formula I, II, III or IV in an amount effective to inhibit PAK1 in a subject.

BRIEF DESCRIPTION OF THE DRAWINGS

FIG. 2. Examples of PAK1 inhibitor compounds selected for further study. IC50 values are shown.

FIG. 3A-3B. Selectivity of Compound C273-0489 for PAK1 against a panel of kinases. A-B show results with different kinases.

FIG. 6A-6B. Selectivity of Compound T813-0242 for PAK1 against a panel of kinases. A-B show results with different kinases.

FIG. 9A-9B. Selectivity of Compound D245-0091 for PAK1 against a panel of kinases. A-B show results with different kinases.

DETAILED DESCRIPTION OF THE INVENTION

Figure 1A:
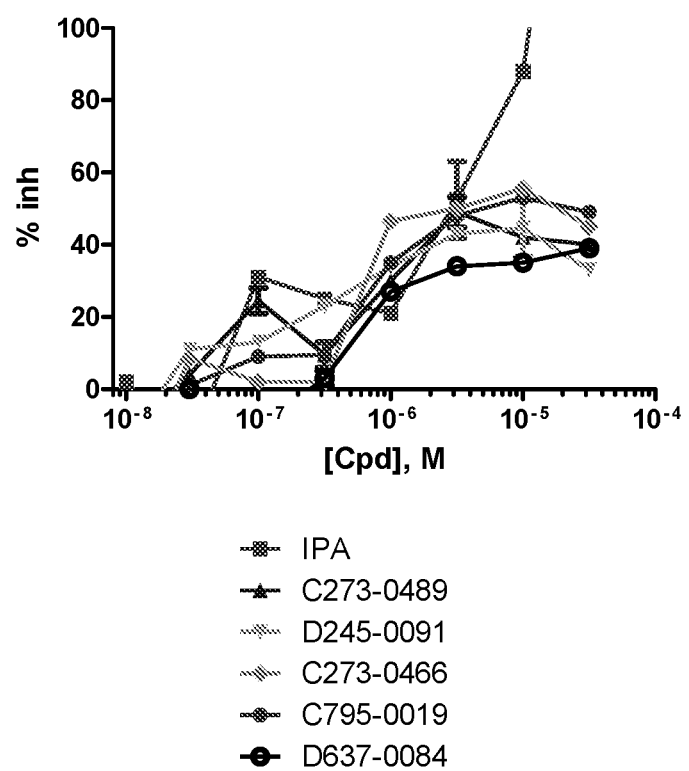
FIG. 1A-1D. Concentration response curves for PAK1 inhibitor compounds. A-D show results with different compounds (Cpd). Results are compared with known PAK1 inhibitor IPA-3.
Figure 1B:
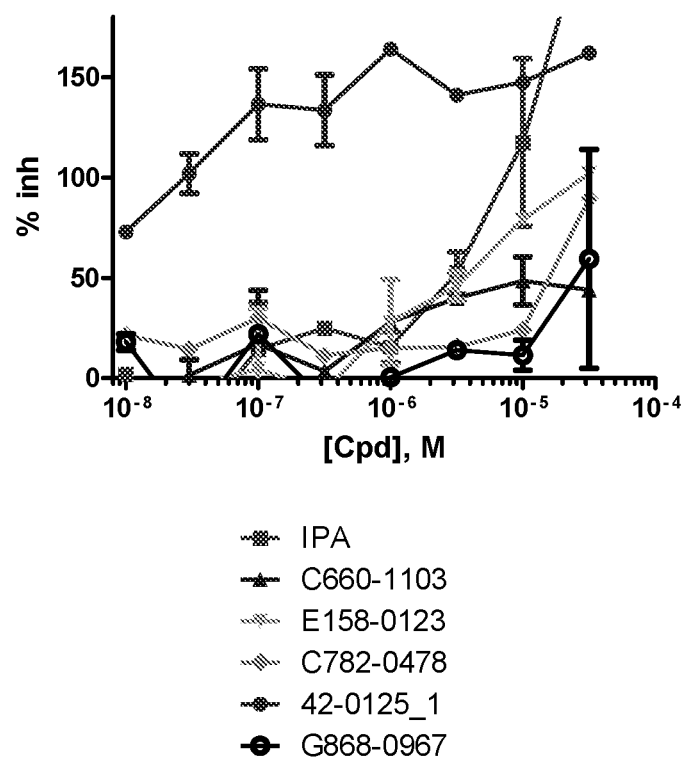
Figure 1C:
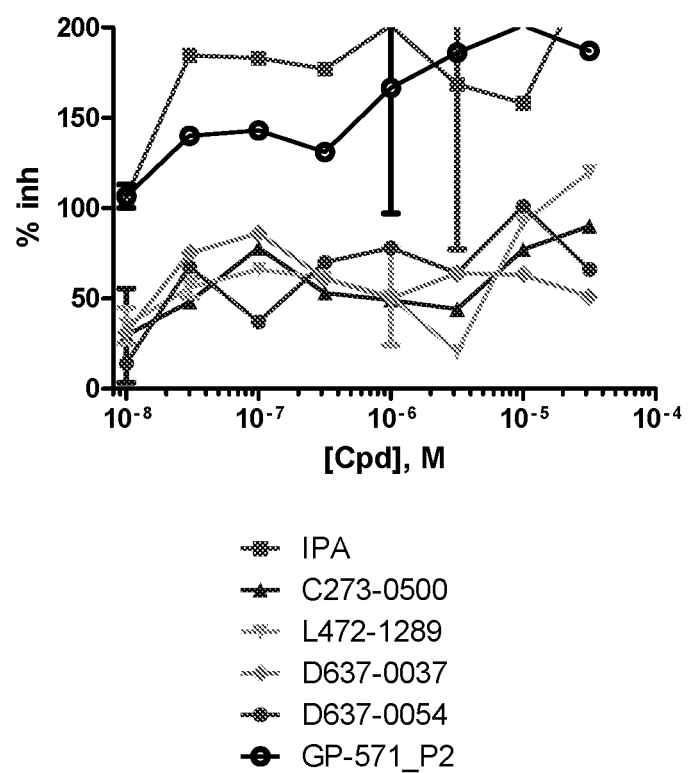
Figure 1D:
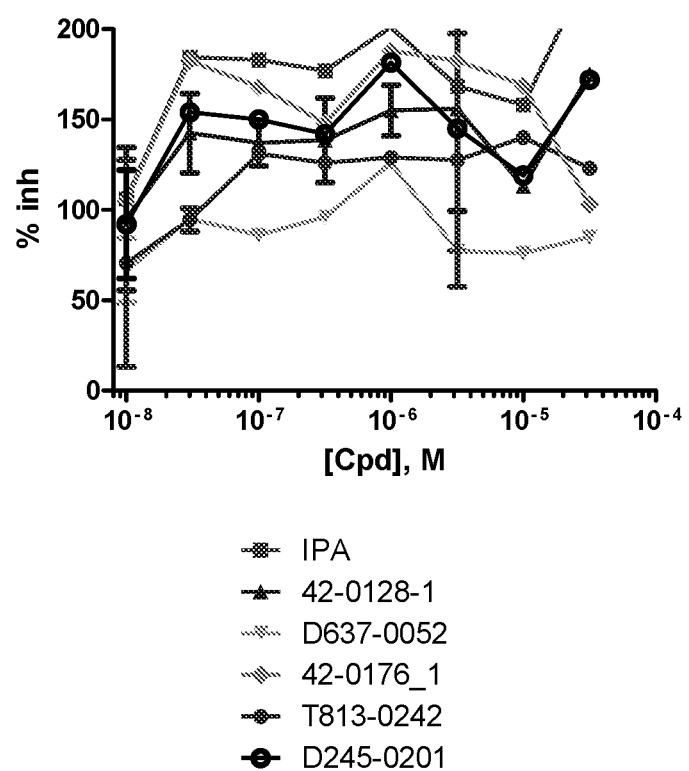

The invention provides a method of treating acute myeloid leukemia (AML), myelodysplastic syndrome (MDS), or a tumor having elevated expression of H2.0-like homeobox (HLX) and/or elevated expression of p21 protein (Cdc42/Rac)-activated kinase (PAK1) in a subject, the method comprising administering to the subject a compound of Formula I, II, III or IV in an amount effective to inhibit PAK1 in a subject.

The invention also provides methods of inhibiting PAK1 in a subject, the methods comprising administering to the subject a compound of Formula I, II, III or IV in an amount effective to inhibit PAK1 in a subject. The subject can be, for example, an individual with elevated expression of PAK1 and/or increased PAK1 activity.

Acute myeloid leukemia (AML) is a cancer of the myeloid line of blood cells, characterized by the rapid growth of abnormal white blood cells that accumulate in the bone marrow and interfere with the production of normal blood cells.

The myelodysplastic syndromes (MDS, formerly known as preleukemia) are a collection of hematological conditions that involve ineffective production (or dysplasia) of the myeloid class of blood cells. Patients with MDS often develop severe anemia and require frequent blood transfusions. In most cases, the disease worsens and the patient develops cytopenias (low blood counts) due to progressive bone marrow failure. In about one third of patients with MDS, the disease transforms into acute myelogenous leukemia (AML), usually within months to a few years. The myelodysplastic syndromes are all disorders of the stem cell in the bone marrow.

In different embodiments, for example, the subject has AML or the subject has MDS. The subject may have elevated expression of HLX. The subject can have, for example, a tumor having elevated expression of HLX or a tumor having elevated expression of HLX and elevated expression of PAK1. In other embodiments, the subject can have a tumor where the activity of PAK1 is increased.

As used herein, elevated expression of HLX and elevated expression of PAK1 means a level that is elevated compared to the level of HLX or PAK1 in a subject who does not have AML, MDS, or a cancer. Similarly, increased PAK1 activity means that the activity of PAK1 is increased compared to the activity level in a subject who does not have AML, MDS, or a cancer.

Examples of cell types for testing PAK1 expression and activity and HLX expression include but are not limited to: 1) tumor bulk cells "blast cells" of an AML or MDS patient, 2) total mononuclear cells from the blood or marrow of an AML or MDS patient, and/or 3) leukemic stem cells of an AML or MDS patient. Controls could include, but are not limited to, for example: total mononuclear cells from the blood or marrow of a healthy donor, CD34 enriched cells from a healthy donor, and/or hematopoietic stem cells from a healthy donor.

In one embodiment of the methods, the HLX or PAK1 expression level or activity level of the gene product thereof is detected using a detectable agent. The detectable agent can be an antibody or a fragment of an antibody, which is itself detectable, e.g. by a secondary antibody, or which is labeled with a detectable marker such as a radioisotope, a fluorophore, a dye etc. permitting detection of the presence of the bound agent by the appropriate machine, or optionally in the case of visually detectable agents, with the human eye. In an embodiment, the amount of detectable agent can be quantified.

Preferably, the PAK1 inhibitor reduces proliferation of AML, MDS and/or tumor cells having elevated expression of HLX and/or PAK1. Preferably, the PAK1 inhibitor induces apoptosis in AML, MDS and/or tumor cells having elevated expression of HLX and/or PAK1. Preferably, the PAK1 inhibitor reduces colony formation of AML, MDS and/or tumor cells having elevated expression of HLX and/or PAK1.

Preferably, treatment of the subject with the PAK1 inhibitor increases survival of the subject compared to untreated control subjects.

As used herein, compounds of Formula I have the structure:

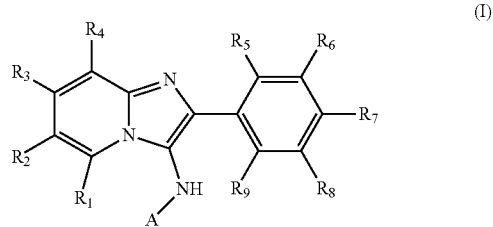

(I)

wherein R1, R2, R3 and R4 of Formula I are independently H, halogen, —OH, —NH$_2$, C1-C6 alkyl, —OCH$_3$, —COCH$_3$, 5- or 6-membered cyclic or heterocyclic, 5- or 6-membered aryl or heteroaryl, wherein the heteroaryl or heterocyclic contains one or more of the same or different heteroatom, or optionally substituted phenyl or benzyl, wherein the phenyl or benzyl is optionally substituted with one or more of halogen, —OH, —NH$_2$, —CH$_3$, or —OCH$_3$;

wherein R5, R6, R7, R8 and R9 of Formula I are independently H, halogen, —OH, —NH$_2$, —NHCH$_3$, —N(CH$_3$)$_2$, C1-C6 alkyl, —OCH$_3$, —SH, —COCH$_3$, —SCH$_3$, 5- or 6-membered cyclic or heterocyclic, 5- or 6-membered aryl or heteroaryl, wherein the heteroaryl or heterocyclic contains one or more of the same or different heteroatom, or optionally substituted phenyl or benzyl, wherein the phenyl or benzyl is optionally substituted with one or more of halogen, —OH, —NH$_2$, —CH$_3$, or —OCH$_3$;

wherein A is a heteroaryl or heterocyclic containing one or more of the same or different heteroatom, or

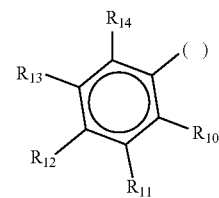

where ( ) represents the point of attachment to the molecular scaffold;

wherein R10, R11, R12, R13 and R14 of Formula I are independently H, halogen, —OH, —NH$_2$, C1-C6 alkyl, —OCH$_3$, —COCH$_3$, 5- or 6-membered cyclic or heterocyclic, or 5- or 6-membered aryl or heteroaryl, wherein the heteroaryl or heterocyclic contains one or more of the same or different heteroatom, and/or R10 and R11, or R11 and R12, or R12 and R13, or R13 and R14 of Formula I together form a 5- or 6-membered hetrocyclic or heteroaryl containing one or more of the same or different heteroatom;

or a pharmaceutically acceptable salt thereof.

Formula II has the structure:

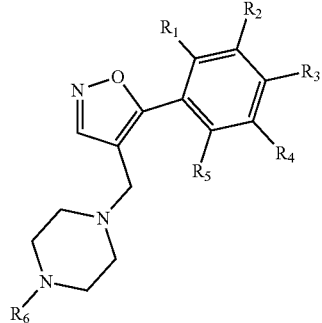
(II)

wherein R1, R2, R3, R4, R5 and R6 of Formula II are independently H, halogen, —OH, —NH$_2$, —NHCH$_3$, —N(CH$_3$)$_2$, C1-C6 alkyl, —OCH$_3$, —COCH$_3$, —SH, or —SCH$_3$, or a pharmaceutically acceptable salt thereof.

Formula III has the structure:

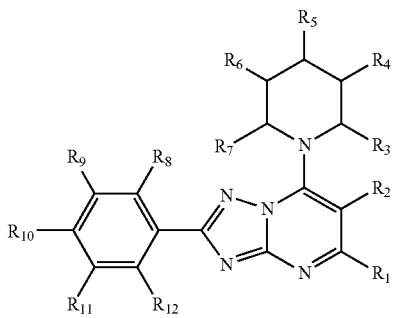
(III)

wherein R1, R2, R3, R4, R5, R6, R7, R8, R9, R10, R11 and R12 of Formula III are independently H, halogen, —OH, —NH$_2$, —NHCH$_3$, —N(CH$_3$)$_2$, C1-C6 alkyl, —OCH$_3$, —COCH$_3$, —SH, or —SCH$_3$, or a pharmaceutically acceptable salt thereof.

Formula IV has the structure:

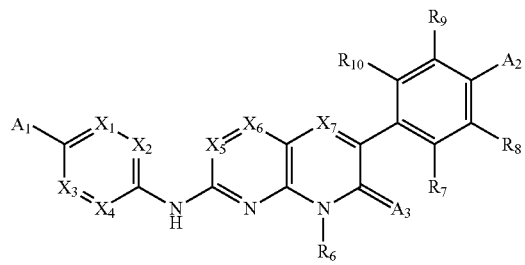
(IV)

wherein A1 and A2 of Formula IV are independently

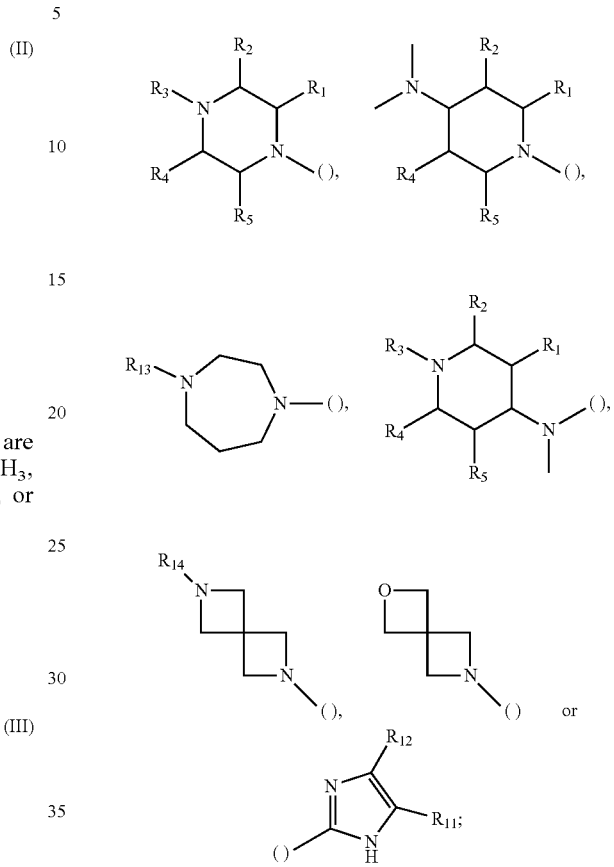

where ( ) represents the point of attachment to the molecular scaffold;

wherein X1, X2, X3, X4, X5 and X7 of Formula IV are independently CH or N;

wherein X6 of Formula IV is CH, N or

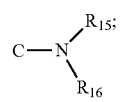

wherein R1, R2, R3, R4, R5, R6, R7, R8, R9, R10, R11, R12, R13, R14, R15 and R16 of Formula IV are independently H, halogen, —OH, —NH$_2$, —NHCH$_3$, —N(CH$_3$)$_2$, C1-C6 alkyl, —OCH$_3$, —COCH$_3$, —SH, or —SCH$_3$;

wherein A3 of Formula IV is O or N, and when A3 is N, R6 is a C2 alkyl that bonds to the N of A3;

or a pharmaceutically acceptable salt thereof.

Regarding Formula I, in different embodiments, one or both of R2 and R6 of Formula I can be, for example, halogen. One or more of R1, R4, R10 and R14 of Formula I can be, for example, —CH$_3$. R7 of Formula I can be, for example, —OH, —OCH$_3$, —N(CH$_3$)$_2$ or —SCH$_3$. R6 or R7 of Formula I can be, for example, is —OCH$_3$. A of Formula I can be, for example, a pyridine, pyrimidine or pyrazine.

In different embodiments, the compound of Formula I can have, for example, Formula Ia or Formula Ib:

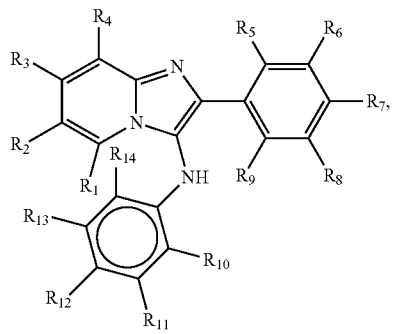
(Ia)

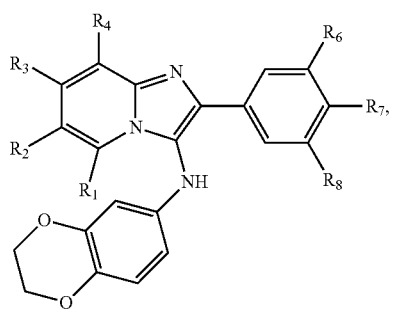
(Ib)

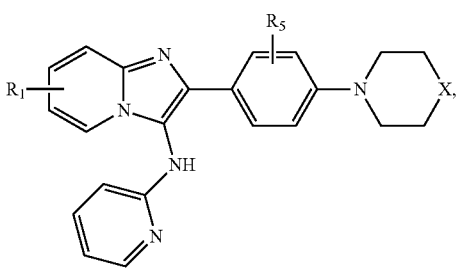
(Ic)

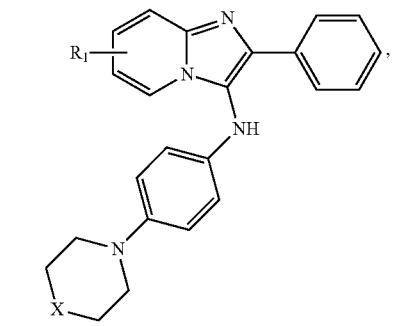
(Id)

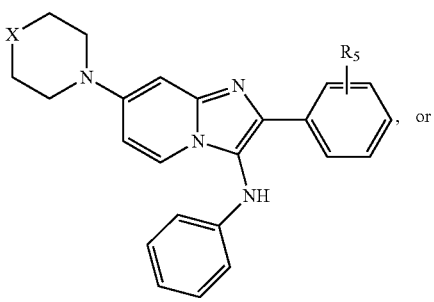
(Ie)

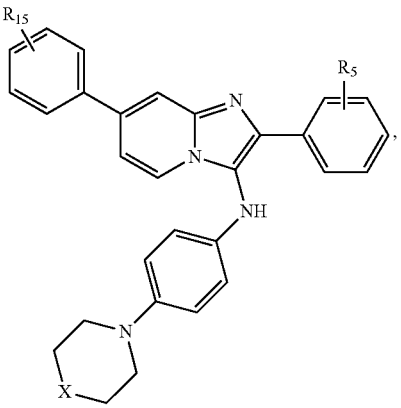
(If)

wherein R1, R2, R3 and R4 are independently H, halogen, —OH, —$NH_2$, —$CH_3$ or —$OCH_3$;

wherein R5, R6, R7, R8 and R9 are independently H, halogen, —OH, —$NH_2$, —$NHCH_3$, —$N(CH_3)_2$, —$CH_3$, —$OCH_3$, —SH or —$SCH_3$;

wherein R10, R11, R12, R13, R14 and R15 are independently H, halogen, —OH, —$NH_2$, —$CH_3$ or —$OCH_3$, wherein any X is independently $CH_2$, NH, O or S, or a pharmaceutically acceptable salt thereof.

Formula IV can have the formula

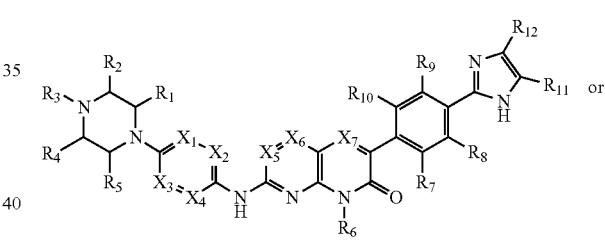
(IVa)

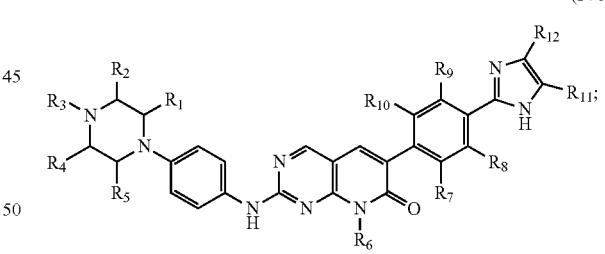
(IVb)

or a pharmaceutically acceptable salt thereof.

Regarding the compound of Formula IV, in one embodiment, X1, X2, X3 and X4 are CH. In another embodiment of the compound of Formula IV, X1 is N, and X2, X3 and X4 are CH. In another embodiment of the compound of Formula IV, X2 is N, and X1, X3 and X4 are CH. In another embodiment of the compound of Formula IV, X1 and X3 are N, and X2 and X4 are CH. In another embodiment of the compound of Formula IV, X5 is N, and X6 and X7 are CH. In another embodiment of the compound of Formula IV, X5 and X7 are N, and X6 is CH. In another embodiment of the compound of Formula IV, X6 is N, and X5 and X7 are CH. In another embodiment of the compound of Formula IV, X5 is N, X7 is CH, and X6 is

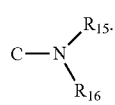

Different examples of the compound of Formula IV include the following:

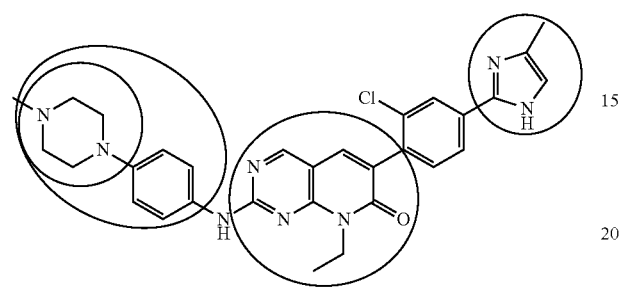

wherein the circle on the left can be any of

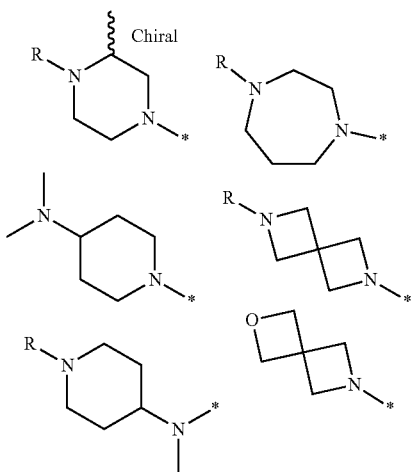

R = Me, Et, i-Pr, c-Pr wherein the ellipse on the left can be any of

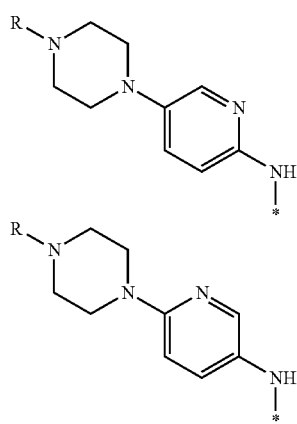

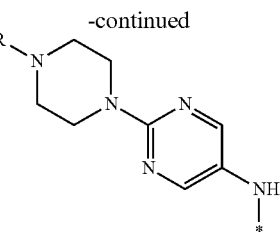

R = Me, Et, i-Pr, c-Pr wherein the circle in the center can be any of

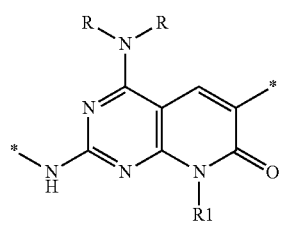

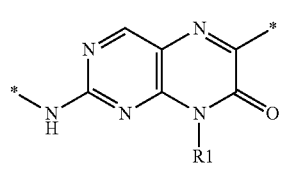

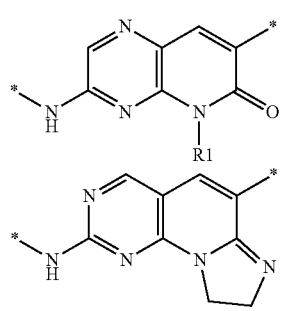

and wherein the circle on the right can any of the structures shown in the circle or ellipse on the left.

In any of the formulas, any halogen can independently be, for example, Br, Cl or I. Any C1-C6 alkyl can independently be, for example —$CH_3$ or —$CH_2CH_3$.

In different embodiments, the compound of Formula I is selected from the group consisting of

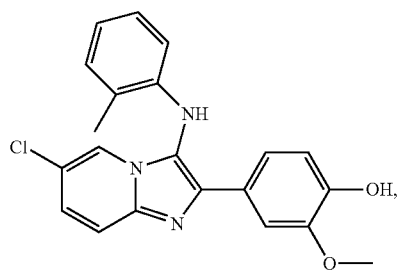

-continued

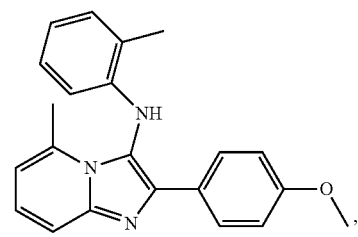

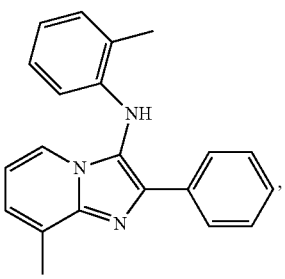

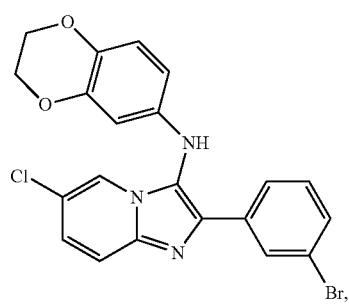

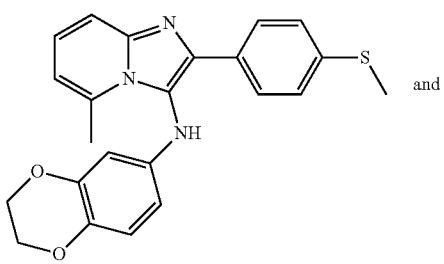

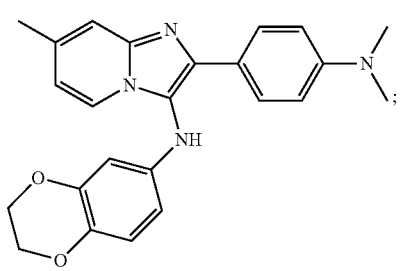

or a pharmaceutically acceptable salt thereof.

The compound of Formula II can have the structure

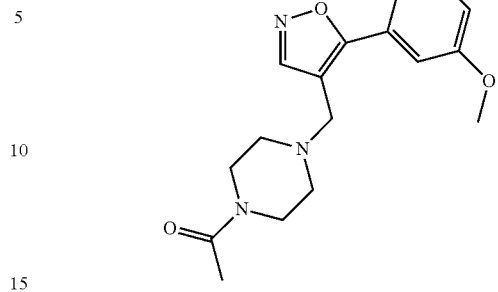

or a pharmaceutically acceptable salt thereof.

The compound of Formula III can have the structure

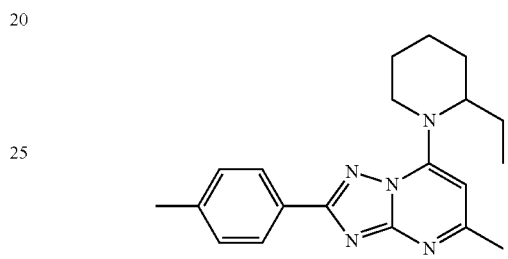

or a pharmaceutically acceptable salt thereof.

The compound of Formula IV can have the structure

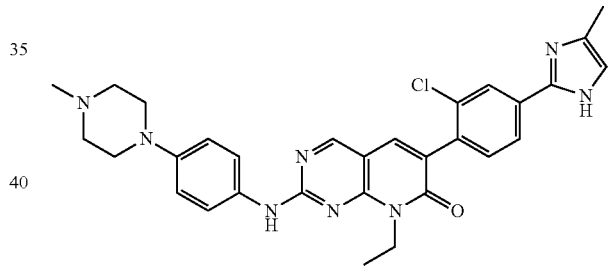

or a pharmaceutically acceptable salt thereof.

In any of the Formula, examples of heterocyclic structures include, but are not limited to, the following:

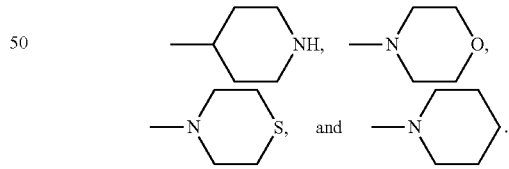

Preferably, the PAK1 inhibitor causes only 0-30% reduction in the activity of PAK2, PAK3, PAK4, PAK5, PAK6 or PAK7 at the same dose that is used to inhibit PAK1. More preferably, the PAK1 inhibitor causes only 0-15% reduction in the activity of PAK2, PAK3, PAK4, PAK5, PAK6 or PAK7 at the same dose that is used to inhibit PAK1. Still more preferably, the PAK1 inhibitor causes only 0-10% reduction in the activity of PAK2, PAK3, PAK4, PAK5, PAK6 or PAK7 at the same dose that is used to inhibit PAK1. Most preferably, the PAK1 inhibitor causes only 0-5% reduction in the activity of PAK2, PAK3, PAK4, PAK5, PAK6 or PAK7 at the same dose that is used to inhibit PAK1.

Also provided is a compound having the structure

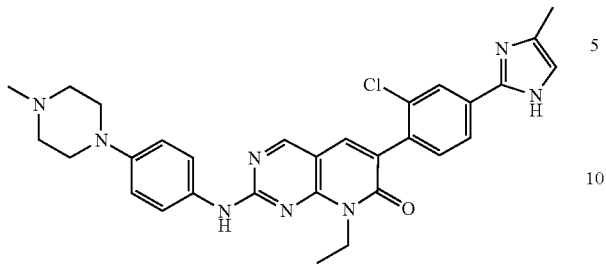

or a pharmaceutically acceptable salt thereof.

As used herein, HLX gene is a human gene encoding H2.0-like homeobox protein. (Convention has upper case "HLX" as the human gene and "Hlx" as non-human equivalents).

The HLX gene has RefSeq Accession no. NM_021958.3.

```
   1  aaaactttgg gagtttttag agacgagttt ttttttttt ctattacttt tcccccccc
  61  taactaacgg actattattg ttgttgtttt aaatttagct cttagggctt agctatttgg
 121  gttttcttgc ggtgtccggc tcccgtctcc ctggctcccc cgcccgccct gcggcccag
 181  cgcccctcgc tctcatccag cccgcgagga gtgcgggcgc cgcgccgcct ttaaagcgag
 241  gccagggagc gaggcggtga ccggccgaga tccggccctc gcctcctccc tcggtggcgc
 301  tagggctccc ggcctctctt cctcagtgcg ggcggagaag cgaaagcgga tcgtcctcgg
 361  ctgccgccgc cttctccggg actcgcgcgc ccctccccgc gcgcccaccc acccagtccg
 421  gctggactgc ggcagccgcg cggctcaccc cggcaggatg ttcgcagccg ggctggctcc
 481  cttctacgcc tccaacttca gcctctggtc ggccgcttac tgctcctcgg ccggcccagg
 541  cggctgctcc ttcccttgg accccgccgc cgtcaaaaag ccctccttct gcatcgcaga
 601  cattctgcac gccggcgtgg gggatctggg ggcggcccg gagggcctgg caggggcctc
 661  ggccgccgcc ctcaccgcgc acttgggctc ggttcacccg cacgcctctt tccaagcggc
 721  ggccagatcc ccgcttcgac ccaccccagt ggtggcgccc tccgaagtcc cggctggctt
 781  cccgcagcgg ctgtctccgc tctcagccgc ctaccaccac catcacccgc aacaacaaca
 841  gcagcagcaa cagccgcagc agcaacagcc tccgcctccg ccccgggctg gcgccctgca
 901  gcccccggcc tcggggacgc gagtggttcc gaaccccccac cacagtggct ctgccccggc
 961  cccctccagc aaagacctca aatttggaat tgaccgcatt ttatctgcag aatttgaccc
1021  aaaagtcaaa gaaggcaaca cgctgagaga tctcacttcc ctgctaaccg gtgggcggcc
1081  cgccggggtg cacctctcag gcctgcagcc ctcggccggc cagttcttcg catctctaga
1141  tcccattaac gaggcttctg caatcctgag tcccttaaac tcgaacccaa gaaattcagt
1201  tcagcatcag ttccaagaca cgtttccagg tccctatgct gtgctcacga aggacaccat
1261  gccgcagacg tacaaaagga agcgttcatg gtcgcgcgct gtgttctcca acctgcagag
1321  gaaaggcctg gagaaaaggt ttgagattca gaagtacgtg accaagccgg accgaaagca
1381  gctggcggcg atgctgggcc tcacggacgc acaggtgaag gtgtggttcc agaaccggcg
1441  gatgaagtgg cggcactcca aggaggccca ggcccaaaag gacaaggaca aggaggctgg
1501  cgagaagcca tcaggtggag cccggctgc ggatggcgag caggacgaga ggagcccag
1561  ccgttctgaa ggcgaggctg agagcgagag cagcgactcc gagtccctgg acatggcccc
1621  cagcgacacg gagcggactg aggggagtga gcgttctctg caccaaacaa cagttattaa
```

-continued

```
1681  ggccccggtc actggcgccc tcattaccgc cagcagtgct gggagtggtg ggagcagcgg
1741  cggcggcggc aatagtttca gcttcagcag cgccagcagt cttagtagca gcagcaccag
1801  tgcgggttgc gccagcagcc ttggcggcgg cggcgcctcg gagcttctcc ctgcaacaca
1861  gcccacagcc agcagcgctc ccaaaagccc cgagccagcc caaggcgcgc ttggctgctt
1921  atagactgta ctagggcgga ggggatccgg gccttgcgtg cagcctccca accatgggct
1981  gggttttgtg cttactgtat gttggcgact tggtagggca ggagacgcag cgtggagcct
2041  acctcccgac attcacgctt cgccccacgc tgctccgact ggctgcagcg gacactgccc
2101  aaagcagagg ggagtctcag tgtcctgcta gccagccgaa cacttctctc cggaagcagg
2161  ctggttcgac tgtgaggtgt ttgactaaac tgtttctctg actcgcccca gaggtcgtgg
2221  ctcaaaggca cttaggacgc cttaaatttg taaataaaat gtttactacg gtttgtaaaa
2281  aaaaaaaaaa aaaaaaaaaa aaaaaaaa
```

(NCBI Reference Sequence: NM_021958.3; SEQ ID NO:1). In an embodiment, each "t" in the above sequence is replaced with a "u."

Human HLX has the amino acid sequence (NCBI Reference Sequence: NP_068777.1, SEQ ID NO:2):

```
  1  mfaaglapfy asnfslwsaa ycssagpggc sfpldpaavk kpsfciadil hagvgdlgaa
 61  peglagasaa altahlgsvh phasfqaaar splrptpvva psevpagfpq rlsplsaayh
121  hhhpqqqqqq qqpqqqqppp ppragalqpp asgtrvvpnp hhsgsapaps skdlkfgidr
181  ilsaefdpkv kegntlrdlt slltggrpag vhlsglqpsa gqffasldpi neasailspl
241  nsnprnsvqh qfqdtfpgpy avltkdtmpq tykrkrswsr avfsnlqrkg lekrfeiqky
301  vtkpdrkqla amlgltdaqv kvwfqnrrmk wrhskeaqaq kdkdkeagek psggapaadg
361  eqderspsrs egeaesessd sesldmapsd tertegsers lhqttvikap vtgalitass
421  agsggssggg gnsfsfssas slssssstsag casslgggga sellpatqpt assapkspep
481  aqgalgcl.
```

PAK1 is p21 protein (Cdc42/Rac)-activated kinase (a serine/threonine-protein kinase enzyme) that in humans is encoded by the PAK1 gene. Human PAK1 has the amino acid sequence (GenBank: AAI09300.1, SEQ ID NO:3):

```
  1  msnngldiqd kppappmrnt stmigagskd agtlnhgskp lppnpeekkk kdrfyrsilp
 61  gdktnkkkek erpeislpsd fehtihvgfd avtgeftgmp eqwarllqts nitkseqkkn
121  pqavldvlef ynskktsnsq kymsftdksa edynssnaln vkaysetpav ppvsededdd
181  dddatpppvi aprpehtksv ytrsvieplp vtptrdvats pisptenntt ppdaltrnte
241  kqkkkpkmsd eeileklrsi vsvgdpkkky trfekigqga sgtvytamdv atgqevaikq
301  mnlqqqpkke liineilvmr enknpnivny ldsylvgdel wvvmeylagg sltdvvtetc
361  mdegqiaavc reclqalefl hsnqvihrdi ksdnillgmd gsvkltdfgf caqitpeqsk
421  rstmvgtpyw mapevvtrka ygpkvdiwsl gimaiemieg eppylnenpl ralyliatng
481  tpelqnpekl saifrdflnr clemdvekrg sakellqhqf lkiakplssl tpliaaakea
541  tknnh.
```

In an embodiment, the compounds described herein are administered in the form of a composition comprising the compound and a carrier. The term "carrier" is used in accordance with its art-understood meaning, to refer to a material that is included in a pharmaceutical composition but does not abrogate the biological activity of pharmaceu- Pharmaceutically acceptable salts that can be used with compounds of the present invention are non-toxic salts derived, for example, from inorganic or organic acids including, but not limited to, salts derived from hydrochloric, sulfuric, phosphoric, acetic, lactic, fumaric, succinic, tartaric, gluconic, citric, methanesulphonic and p-toluenesulphonic acids.

tically active agent(s) that are also included within the composition. Typically, carriers have very low toxicity to the animal to which such compositions are to be administered. In some embodiments, carriers are inert. Pharmaceutically acceptable carriers and diluents that can be used herewith encompasses any of the standard pharmaceutical carriers or diluents, such as, for example, a sterile isotonic saline, phosphate buffered saline solution, water, and emulsions, such as an oil/water or water/oil emulsions.

The compounds and compositions of the present invention can be administered to subjects using routes of administration known in the art. The administration can be systemic or localized to a specific site. Routes of administration include, but are not limited to, intravenous, intramuscular, intrathecal or subcutaneous injection, oral or rectal administration, and injection into a specific site.

All combinations of the various elements described herein, including all subsets, are within the scope of the invention unless otherwise indicated herein or otherwise clearly contradicted by context. Where a numerical range is provided herein for any parameter, it is understood that all numerical subsets of that numerical range, and all the individual integer values contained therein, are provided as part of the invention. Thus, C1-C6 alkyl includes, for example, the subset of alkyls which are 1-3 carbon atoms, the subset of alkyls which are 2-5 carbon atoms etc. as well as an alkyl which has 1 carbon atom, an alkyl which has 3 carbon atoms, an alkyl which has 6 carbon atom, etc.

Specifically excluded from Formula I, II, III and IV are any compounds that were known to be inhibitors of PAK1 at the time of the filing of the present application.

The subject can be any animal such as, for example, a farm animal or veterinary animal, and is preferably a human.

This invention will be better understood from the Experimental Details, which follow. However, one skilled in the art will readily appreciate that the specific methods and results discussed are merely illustrative of the invention as described more fully in the claims that follow thereafter.

Experimental Details

Summary

Inhibition of PAK1 for treatment of AML and MDS has been described (U.S. Patent Application Publication Nos. 2015/0299336 A1 and 2015/0359815 A1). The present invention addresses the need for small molecule treatments for AML and MDS as well as for tumors expressing elevated levels of HLX and for other conditions in which it is desirable to inhibit PAK1.

Materials and Methods

Human AML cell lines THP1 and MOLM13 were cultured under standard conditions. For cell proliferation assays, manual cell counts were performed by culturing cells in 24- or 48-well plates. Viable cells were counted using trypan blue exclusion and cell density was re-adjusted in each well every 3-5 days. For cell cycle assays, the Click-iT™ EdU Flow Cytometry Assay system (Invitrogen) was used following the manufacturer's instructions. For apoptosis assays, apoptotic and necrotic cells were analyzed by use of Annexin V/DAPI staining.

Compounds were screened for PAK1 inhibition using a 50,024 compound library by ChemDiv (San Diego, Calif.). Protocol for PAK1 compound primary screen at [ATP]10× Km; [PAK1]=1 ng Materials 384-well Black Low volume non-binding plates (Cat #4514, Corning), 96-well plates with well volume of up to 300 µL (Corning), multi-channel pipettor (12 channels) or any pipetting device that can accurately deliver repeated volumes of 2.5 µl and 5 µl.

Reagents

| Z'-LYTE ® Kinase Assay Kit | | | |
|---|---|---|---|
| Component | Description | Qty | Cat # |
| Z'-LYTE ®Ser/Thr 19 peptide Substrate | 1 mM in 99% DMSO; 0.1% Formic Acid; 0.9% water | 20 µL | PV4530 |
| Z'-LYTE ®Ser/Thr 19Phospho-peptide | 1 mM in 99% DMSO; 0.1% Formic Acid; 0.9% water | 10 µL | PV4531 |
| 5X Kinase Buffer | 250 mM HEPES (pH 7.5); 50 mM MgCl$_2$; 5 mM EGTA; 0.05% Brij-35 | 4 mL | PV3189 |
| ATP | 10 mM in water | 0.5 mL | PV3227 |
| Development Reagent | Proprietary | 50 µL | PV3295 |
| Development Buffer | Proprietary | 5 mL | P3127 |
| Stop Reagent | Proprietary | 5 mL | P3094 |
| PAK-1 | 370 µg/ml in 50 mM Tris, pH 7.5, 150 mM NaCl, 0.5 mM EDTA, 0.02% Triton X-100, 2 mM DTT, 50% glycerol | 100 µg | PR7402A |

Prepare Reagents

Note: Thaw and store the kinase and Development Reagent on ice prior to preparation of dilutions. Equilibrate all other assay components to room temperature.

1. 1.33× Kinase Buffer

Dilute 2 ml of 5× Kinase Buffer to 1.33× with water and any required kinase supplements. In the screen, because the test compounds are in 4% DMSO, the 10 µl kinase reaction will contain all the kinase components in 1× Kinase Buffer and 1% DMSO.

2. 4× Test Compounds

Prepare single concentrations of the test compounds in 4% DMSO (in water) at four times the concentrations desired in the 10-µl kinase reactions. For an array of wells, A to H by 1 to 12, add 48 µl of water to wells A2-H10, add 2 µl of compound (in DMSO) to wells A2-H10 (to get 25-fold dilution which equals 4%).

3. Kinase/Z'-LYTE® Peptide Substrate Mixture

Prepare 2000 µl of a kinase/Z'-LYTE® Ser/Thr 19 Peptide Substrate Mixture by diluting the kinase to 2× the empirically previously determined optimal concentration (1 ng/10 µl=0.1 ng/µl, 2×=0.2 ng/µl) and the Z'-LYTE® Ser/Thr 19 Peptide Substrate to 4 µM (8 µl) in 1.33× kinase buffer. Add µl of PAK1 to 1992 µl of 1.33× kinase buffer, add 8 µl of Z'-LYTE® Ser/Thr 19 Peptide Substrate to the mixture from the previous step, mix gently by pipetting; do not vortex.

4. Phospho-Peptide Solution

Add 2 µl of Z'-LYTE® Ser/Thr 19 Phospho-peptide to 498 µl of 1.33× kinase buffer. Mix thoroughly.

5. ATP Solution

Prepare 1110 µl of an ATP solution by diluting the 10 mM ATP in 1.33× kinase buffer to 4× the desired ATP concentration (500 µM).

6. Development Solution

Prepare Development Solution as specified in the Development Reagent Certificate of Analysis included with kit.

Assay Protocol

1. Kinase Reaction (Primary Reaction)

Add each component in the following order at the appropriate time points according to the table below:

|  | Assay Reaction(s) | Controls | | |
|---|---|---|---|---|
| Reagents | Kinase + Test Compound | 100% Inhibition (no ATP) | 0% Inhibition (with ATP) | 100% Phosphorylation |
| Kinase Reaction (Primary Reaction) | | | | |
| Step 1 | | | | |
| 4X Test Compound (4% DMSO) | 2.5 μl | | | |
| 4% DMSO | | 2.5 μl | 2.5 μl | 2.5 μl |
| Kinase/Z'-LYTE ™ Peptide Substrate Mixture | 5 μl | 5 μl | 5 μl | |
| Z'-LYTE ™ Phospho-peptide Solution | | | | 5 μl |
| 1.33X Kinase Buffer | | 2.5 μl | | 2.5 μl |
| 4X ATP Solution | 2.5 μl | | 2.5 μl | |

For an array of wells, A to P by 1 to 24, add 2.5 μl of 4× Test Compound (4% DMSO) to wells A4-P21, add 2.5 μl of 4% DMSO to wells A3-P3, add 5 μl of Kinase/Z'-LYTE® Peptide Substrate Mixture to wells A3-J3 and A4-P21, add 5 μl of Z'-LYTE® Phospho-peptide Solution to wells K3-O3, add 2.5 μl of 1.33× Kinase Buffer to wells A3-E3 and K3-O3, initiate reaction by adding 2.5 μl of 4× ATP Solution to wells F3-J3 and A4-P21, mix contents of wells of assay plate and incubate the 10 μl Kinase Reaction for 1 hour at room temperature.

Note: The Kinase Reaction contains 1× inhibitor, 1× Kinase, 1× ATP, and 2 μM Z'-LYTE® Ser/Thr 19 Peptide Substrate.

2. Development Reaction (Secondary Reaction)

Add 5 μl of Development Solution to all working wells, mix contents of wells of assay plate and incubate the 15 μl development reaction for 1 hour at room temperature.

3. Stop Step and Fluorescence Detection

Add 5 μl of Stop Reagent to all working wells, mix contents of wells of assay plate and measure fluorescence signals.

Note: The 20-μl (final volume) assay contains 1 μM Z'-LYTE® Ser/Thr 19 Peptide Substrate.

Protocol for determining IC50 Values for test compounds at [ATP]=10×Km; [PAK1]=1 ng Materials 384-well Black Low volume non-binding plates (Cat #4514, Corning), 96-well plates with well volume of up to 300 μL (Corning), multi-channel pipettor (12 channels) or any pipetting device that can accurately deliver repeated volumes of 2.5 μl and 5 μl.

Reagents

| Z'-LYTE ® Kinase Assay Kit | | | |
|---|---|---|---|
| Component | Description | Qty | Cat # |
| Z'-LYTE ®Ser/Thr 19 peptide Substrate | 1 mM in 99% DMSO; 0.1% Formic Acid; 0.9% water | 20 μL | PV4530 |
| Z'-LYTE ®Ser/Thr 19 Phospho-peptide | 1 mM in 99% DMSO; 0.1% Formic Acid; 0.9% water | 10 μL | PV4531 |
| 5X Kinase Buffer | 250 mM HEPES (pH 7.5); 50 mM MgCl$_2$; 5 mM EGTA; 0.05% Brij-35 | 4 mL | PV3189 |
| ATP | 10 mM in water | 0.5 mL | PV3227 |
| Development Reagent | Proprietary | 50 μL | PV3295 |
| Development Buffer | Proprietary | 5 mL | P3127 |
| Stop Reagent | Proprietary | 5 mL | P3094 |
| PAK-1 | 370 μg/ml in 50 mM Tris, pH 7.5, 150 mM NaCl, 0.5 mM EDTA, 0.02% Triton X-100, 2 mM DTT, 50% glycerol | 100 μg | PR7402A |

Prepare Reagents

Note: Thaw and store the kinase and Development Reagent on ice before preparing dilutions. Equilibrate all other assay components to room temperature.

1. Kinase Reaction Buffer

Add 2 ml 5× Kinase Buffer to 8 ml water to prepare 5 ml of Kinase Buffer A.

2. Test Compounds

Thaw the concentrated stock of test compound at room temperature.

2.1. Add 10 μl of 100% DMSO to row A, columns 2-11 (wells A2-A11) in a 96-well assay plate (non-binding surface). To well A1, add 15 μl of the concentrated stock of test compound. This will be the highest concentration of test compound in a 10-point titration curve. Use a concentration that is 100× the final desired 1× concentration per 10 µl kinase reaction. For example, if the final 1× concentration of 100 µM is desired for the highest concentration of test compound in the 10 point titration curve, add 15 µl of 10 mM test compound to well A1.

2.2. Titrate the 100× test compound three-fold across the assay plate from well A1 to well A10. To perform this threefold titration, transfer 5 µl of the 100× test compound from well A1 to the 10 µl of 100% DMSO in well A2. Repeat for wells A2-A10. Discard the final 5 µl from well A10 so that all wells contain 10 µl. Do not titrate the compound into wells A11 and A12, because these will be vehicle-only (DMSO) control for the 0% inhibition, 0% phosphorylation, and 100% phosphorylation controls. This completes the 10-point three-fold titration of test compound at 100× concentration.

2.3. Transfer a 2 µl aliquot of the 100× test compound titration series from each well in row A of the 96-well assay plate (wells A1-A12) to row B (wells B1-B12). Add 48 µl of complete kinase reaction buffer to each well in row B to dilute the 100× three-fold titration series of test compound to 4× (the DMSO will also be diluted, to 4%).

2.4. Transfer 2.5 µl of the 4× concentrated three-fold titration series of test compound from row B of the 96-well assay plates to quadruplicate wells of a 384-well assay plate. Each well in columns 21-24 should contain 2.5 µl of 4% DMSO (no compound) in complete kinase reaction buffer. This 2.5 µl addition of 4× test compound in 4% DMSO produces a 1× concentration of test compound in 1% DMSO for a 10 µl kinase reaction.

2.5. Dispense 2.5 µl of complete kinase reaction buffer to each well in columns 23-24 of the 384-well assay plate.

Prepare Reagents

1. Prepare 500 µl of 4 µM Z'-LYTE® Phospho-peptide by adding 2 µl of 1 mM Z'-LYTE® Phospho-peptide to 498 µl of complete kinase reaction buffer.
2. Dispense 5 µl of the 4 µM Z'-LYTE® Phospho-peptide (2×) to each well in column 24 of the 384-well assay plate.
3. Prepare 1000 µl of 4 µM Z'-LYTE® Peptide Substrate (2×)/2× kinase solution in complete kinase reaction buffer. If necessary, prepare an intermediate dilution of the kinase in complete kinase reaction buffer before preparing the Z'-LYTE™ Peptide Substrate (2×)/2× kinase solution. Use the appropriate 2× kinase concentration in the assay to phosphorylate 20-50% of the 0% inhibition controls at the ATP concentration desired.
4. Dispense 5 µl of the Z'-LYTE® Peptide Substrate (2×)/2× kinase solution to each well in columns 1-23.
5. Prepare 1000 µl of 4× ATP in complete kinase reaction buffer. Use the appropriate 4× ATP concentration at the desired kinase concentration to achieve 20-50% phosphorylation of the 0% inhibition controls in the assay.
6. Dispense 2.5 µl of the 4× ATP in complete kinase reaction buffer to each well in columns 1-22.
7. Shake the assay plate on a plate shaker for 30 seconds to mix the reactions thoroughly.
8. Incubate the assay plate for one hour at room temperature (20-25° C.).

Prepare Development Solution

1. Prepare Development Solution as specified in the Development Reagent Certificate of Analysis included with this kit. The Certificate of Analysis indicates the correct dilution for each lot of Development Reagent into Development Buffer. Dilution factors for the Development Reagent can vary from lot to lot.
2. Add 5 µl of Development Solution to each well in the 384-well assay plate.
3. Shake the assay plate on a plate shaker for 30 seconds to mix the reactions thoroughly.
4. Incubate the assay plate for one hour at room temperature (20-25° C.).

Stop Step and Fluorescence Detection

1. Add 5 µl of Stop Reagent to each well in the 384-well assay plate.
2. Shake the assay plate on a plate shaker for 30 seconds to mix the reactions thoroughly.
3. Measure the coumarin and fluorescein emission signals on a fluorescence plate reader (excitation: 400 nm; emission 445 and 520 nm, respectively).

Analyze Data

1. Calculate the emission ratio for each sample and control well.
2. Calculate the percent phosphorylation for each sample well and control well.
3. Calculate the percent inhibition for each sample well in the inhibitor titration series using the following equation:

$$\text{percent inhibition} = 100 \times \left(1 - \frac{\text{percent phosphorylation of test compound well}}{\text{percent phosphorylation of 0\% inhibition control}}\right).$$

4. Graph the percent inhibition (y-axis) versus the log concentration of the text compound (x-axis) using an appropriate graphing software program. From this graph, calculate the test compound concentration that inhibits kinase activity by 50% (the IC50 value).

Chemical Syntheses

C273 Series

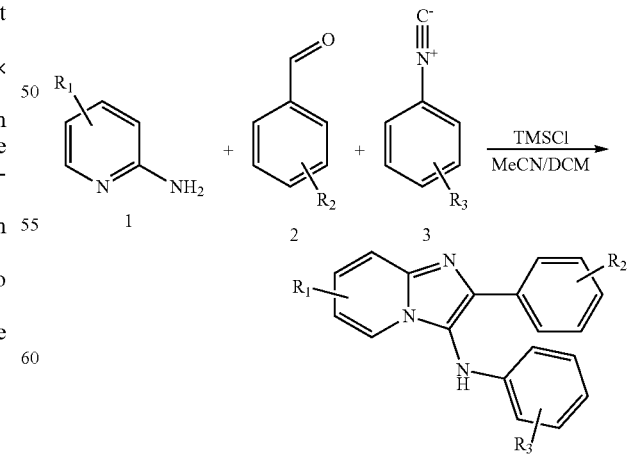

General procedure. Analytical thin layer chromatography (TLC) was performed with Sorbfil TLC plates. Visualization was accomplished by irradiation under a 254 nm UV lamp. $^1$H and $^{13}$C NMR spectra, at 400 and 100 MHz, respectively, were recorded with a Bruker DPX-400 spectrometer; chemical shifts are reported in ppm with the solvent resonance as the internal standard (CDCl$_3$ 7.26 ppm, dimethyl sulfoxide (DMSO-d$_6$) 2.49 ppm. The following abbreviations are used in NMR spectra descriptions: s=singlet, d=doublet, t=triplet, q=quartet, m=multiplet, br=broad. IUPAC nomenclature is used for atom numbering. Purifies of all synthesized compounds were confirmed by LC-MS analysis performed with a Shimadzu HPLC instrument with PE SCIEX API 150EX mass- and Shimadzu UV—(254 and 215 nm) detectors. Separation was achieved with a XBridge C18 3.5μ (4.6*100 mm) column with use of a gradient (5-95%) of acetonitrile in water both with 0.05% TFA over 10 min at 0.9 mLmin$^{-1}$.

The starting amine 1 and an aldehyde 2 in equimolar amounts was mixed in anhydrous MeCN and the resulting solution was heated at reflux for 2 h to ensure complete formation of the respective imine intermediate. The reaction mixture was then cooled to room temperature and evaporated to dryness. The solid residue was further dried by addition of toluene and concentration of the resulting suspension in vacuo (repeated twice). The residue was then suspended in anhydrous MeCN and treated with a solution of an equimolar amount of TMSCl in anhydrous DCM. The mixture was stirred at ambient temperature for 30 min (in most cases the suspension cleared), and then treated with a solution of isocyanide 3 (1 equiv) in MeCN and heated at 70° C. overnight. At this stage, all of the reactions described herein were complete by LCMS analyses (as judged by the disappearance of 1). In a number of cases the products isolated by filtration were at least 90% pure as judged from LCMS and 1H NMR data. In some cases, chromatographic isolation of the products was required (silica gel, eluted by appropriate gradients of 0-10% methanol in dichloromethane).

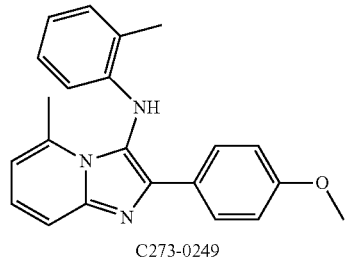 [SMILES: COc1ccc(-c2nc3cccc(C)n3c2Nc2ccccc2C)cc1]

C273-0249

2-(4-Methoxyphenyl)-5-methyl-N-(o-tolyl)imidazo[1,2-a]pyridin-3-amine. $^1$H NMR (400 MHz, DMSO-d$_6$) δ ppm: 7.96; (d, J=8.93 Hz, 2H), 7.41-7.45; (m, 2H), 7.12-7.16; (m, 2H), 6.93; (d, J=8.93 Hz, 2H), 6.86; (t, J=7.82 Hz, 1H), 6.56-6.62; (m, 2H), 5.85; (d, J=7.82 Hz, 1H), 3.73; (s, 3H), 2.60; (s, 3H), 2.33; (s, 3H). LCMS m/z 344.4 (M+H)$^+$ Rt 5.73 min.

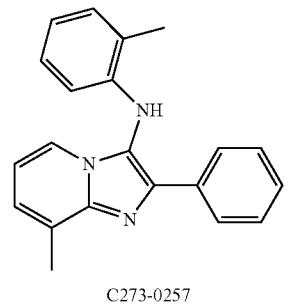 [SMILES: Cc1ccccc1Nc1c(-c2ccccc2)nc2c(C)cccn12]

C273-0257

8-Methyl-2-phenyl-N-(o-tolyl)imidazo[1,2-a]pyridin-3-amine. $^1$H NMR (400 MHz, DMSO-d$_6$) δ ppm: 8.06; (d, J=7.34 Hz, 2H), 7.77; (d, J=6.60 Hz, 1H), 7.52; (s, 1H), 7.37; (t, J=7.46 Hz, 2H), 7.26; (t, J=7.21 Hz, 1H), 7.13; (dd, J=12.59, 6.72 Hz, 2H), 6.82; (q, J=13.57, 6.72 Hz, 2H), 6.84; (t, J=7.21 Hz, 1H), 5.86; (d, J=7.95 Hz, 1H), 2.58; (s, 3H), 2.41; (s, 3H). LCMS m/z 314.4 (M+H)$^+$ Rt 5.58 min.

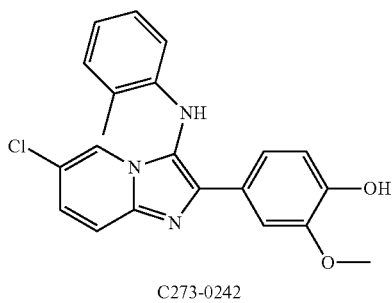

C273-0242

4-(6-Chloro-3-(o-tolylamino)imidazo[1,2-a]pyridin-2-yl)-2-methoxyphenol. $^1$H NMR (400 MHz, DMSO-d$_6$) δ ppm: 9.10; (s, 1H), 8.14; (s, 1H), 7.66; (d, J=9.54 Hz, 1H), 7.52; (s, 1H), 7.47-7.45; (m, 2H), 7.33; (dd, J=9.41, 2.08 Hz, 1H), 7.16; (d, J=7.21 Hz, 1H), 6.84; (t, J=7.46 Hz, 1H), 6.77; (d, J=8.31 Hz, 1H), 6.66; (t, J=7.46 Hz, 1H), 5.88; (d, J=7.95 Hz, 1H) 3.58; (s, 3H), 2.41; (s, 3H). LCMS m/z 380.3 (M+H)$^+$ Rt 5.41 min.

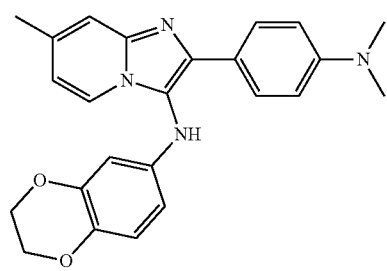

C273-0466

N-(2,3-dihydrobenzo[b][1,4]dioxin-6-yl)-2-(4-(dimethylamino)phenyl)-7-methylimidazo[1,2-a]pyridin-3-amine. $^1$H NMR (400 MHz, DMSO-d$_6$) δ ppm: 7.88; (d, J=8.68 Hz, 2H), 7.77; (d, J=6.72 Hz, 1H), 7.73; (s, 1H), 7.30; (s, 1H), 6.69-6.73; (m, 3H), 6.64; (d, J=6.68 Hz, 1H), 6.00; (dd, J=8.56, 2.69 Hz, 1H), 5.90; (d, J=2.45 Hz, 1H), 4.12; (m, 4H), 2.90; (s, 6H), 2.35; (s, 3H). LCMS m/z 401.3 (M+H)$^+$ Rt 5.41 min.

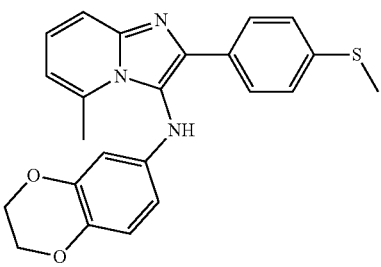

C273-0489

N-(2,3-dihydrobenzo[b][1,4]dioxin-6-yl)-5-methyl-2-(4-(methylthio)phenyl)imidazo[1,2-a]pyridin-3-amine. $^1$H NMR (400 MHz, DMSO-d$_6$) δ ppm: 8.01; (d, J=8.44 Hz, 2H), 7.74; (s, 1H), 7.42; (d, J=8.80 Hz, 1H), 7.27; (d, J=8.44 Hz, 2H), 7.15; (dd, J=8.80, 6.85 Hz, 1H), 6.66; (d, J=8.56 Hz, 1H), 6.59; (d, J=7.21 Hz, 1H), 5.83-5.94; (m, 2H), 4.12; (m, 4H), 2.66; (s, 6H), 2.47; (s, 3H). LCMS m/z 404.5 (M+H)$^+$ Rt 5.58 min.

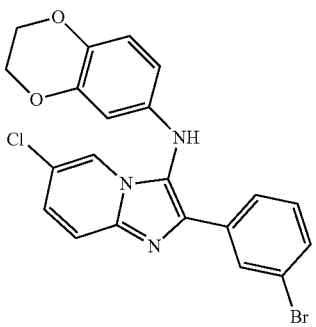

C273-0500

2-(3-Bromophenyl)-6-chloro-N-(2,3-dihydrobenzo[b][1,4]dioxin-6-yl)imidazo[1,2-a]pyridin-3-amine. $^1$H NMR (400 MHz, DMSO-d$_6$) δ ppm: 8.21; (s, 1H), 8.10; (s, 1H), 8.03; (d, J=7.95 Hz, 1H), 7.98; (s, 1H), 7.69; (d, J=9.66 Hz, 1H), 7.50; (d, J=8.07 Hz, 1H), 7.37; (m, 2H), 6.67; (d, J=9.29 Hz, 1H), 6.00; (m, 2H), 4.14; (m, 4H). LCMS m/z 458.1 (M+H)$^+$ Rt 6.43 min.

D245-0091

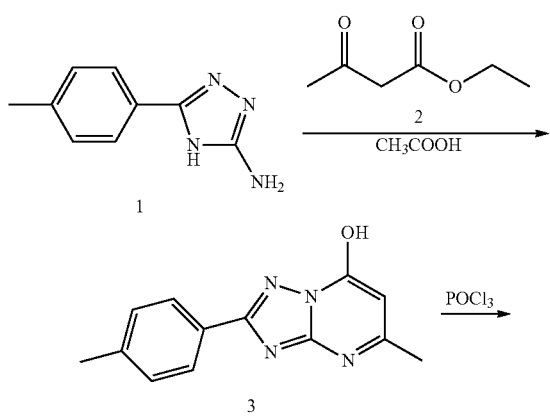

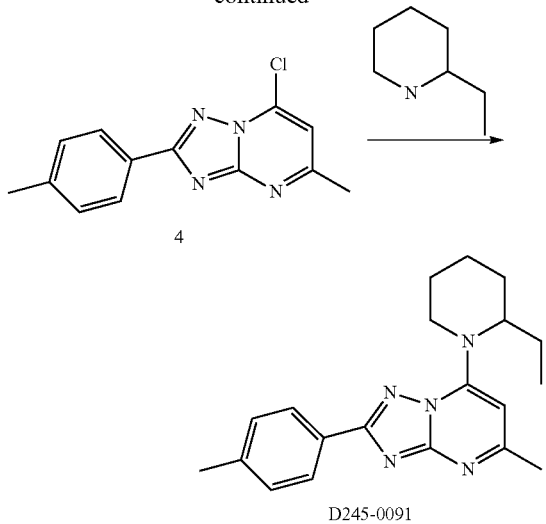

D245-0091

General procedure. Analytical thin layer chromatography (TLC) was performed with Sorbfil TLC plates. Visualization was accomplished by irradiation under a 254 nm UV lamp. $^1$H and $^{13}$C NMR spectra, at 400 and 100 MHz, respectively, were recorded with a Bruker DPX-400 spectrometer; chemical shifts are reported in ppm with the solvent resonance as the internal standard (CDCl$_3$ 7.26 ppm, dimethyl sulfoxide (DMSO-d$_6$) 2.49 ppm. The following abbreviations are used in NMR spectra descriptions: s=singlet, d=doublet, t=triplet, q=quartet, m=multiplet, br=broad. IUPAC nomenclature is used for atom numbering. Purities of all synthesized compounds were confirmed by LC-MS analysis performed with a Shimadzu HPLC instrument with PE SCIEX API 150EX mass- and Shimadzu UV—(254 and 215 nm) detectors. Separation was achieved with a XBridge C18 3.5µ (4.6*100 mm) column with use of a gradient (5-95%) of acetonitrile in water both with 0.05% TFA over 10 min at 0.9 mLmin$^{-1}$.

Compound 3. Compound 1 (0.5 mol) was dissolved in glacial acetic acid (150 mL) with heating and compound 2 (0.75 mol) was added. The mixture was refluxed for about 6 hours. The reaction mixture was cooled down and the precipitate was filtered off. The product was crystallized from isopropanol. Yield of compound 3 was 77% (70 g).

Compound 4. Compound 3 (0.3 mol) was added to POCl$_3$ (0.3 mol) and the mixture was refluxed for 3 hours. POCl$_3$ was removed in vacuo and chloroform (300 mL) was added to the residue. The solution was poured into water containing ice, neutralized with saturated aqueous NaHCO$_3$ to pH=8, the organic layer was separated, washed with water, dried over MgSO$_4$ and concentrated in vacuo. The residue was crystallized from benzene. Yield of compound 4 was 60%.

D245-0091 7-(2-Ethylpiperidin-1-yl)-5-methyl-2-(p-tolyl)-[1,2,4]triazolo[1,5-a]pyrimidine. Compound 4 (0.5 g) was dissolved in benzene (30 mL) with heating and compound 5 (stoichiometric amount) was added. The mixture was refluxed for 0.5 hour, benzene was removed in vacuo, and the residue was crystallized from isopropanol. Yield of compound D245-0091 was 65%. $^1$H NMR (400 MHz, DMSO-d$_6$) δ ppm: 8.05; (d, J=8.07 Hz, 2H), 7.35; (d, J=8.07 Hz, 2H), 6.47; (s, 1H), 5.03; (br. s, 1H), 4.13; (d, J=11.86 Hz, 1H), 3.35; (m, 1H), 2.45; (s, 3H), 2.37; (s, 3H), 1.59-1.86; (m, 8H), 0.83; (t, J=7.34 Hz, 3H). LCMS m/z 336.5 (M+H)$^+$ Rt 6.85 min.

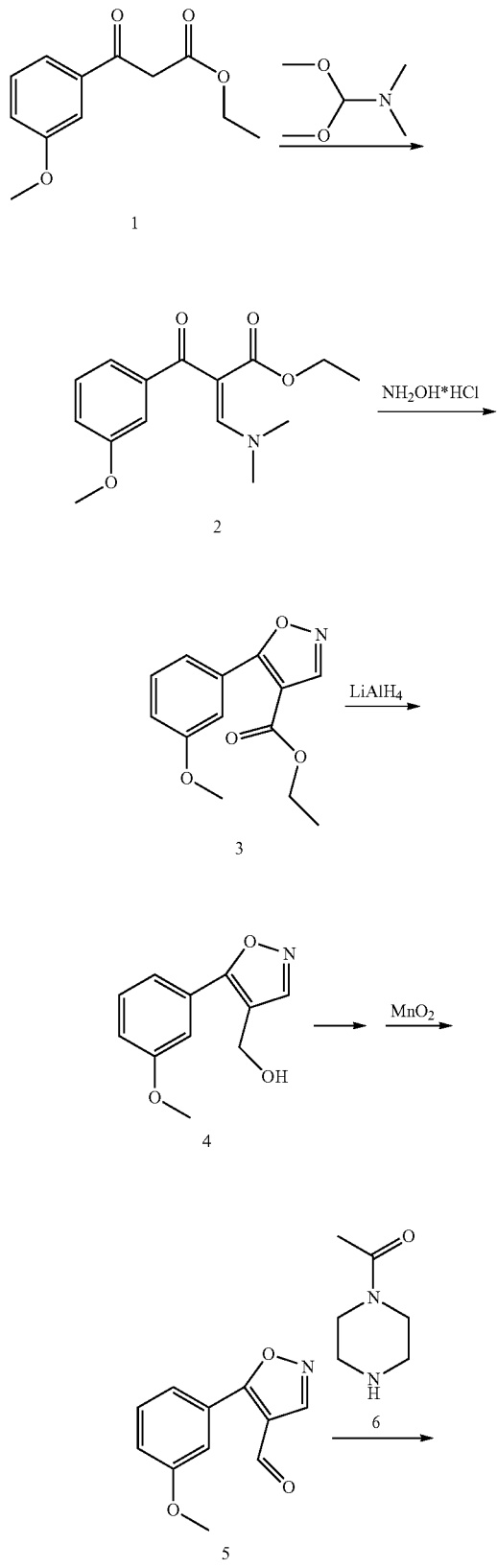
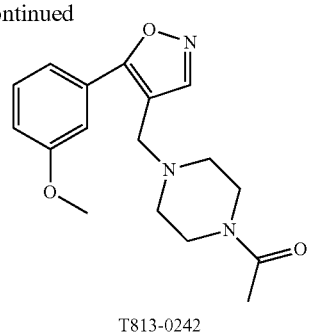

General procedure. Analytical thin layer chromatography (TLC) was performed with Sorbfil TLC plates. Visualization was accomplished by irradiation under a 254 nm UV lamp. $^1$H and $^{13}$C NMR spectra, at 400 and 100 MHz, respectively, were recorded with a Bruker DPX-400 spectrometer; chemical shifts are reported in ppm with the solvent resonance as the internal standard (CDCl$_3$ 7.26 ppm, dimethyl sulfoxide (DMSO-d$_6$) 2.49 ppm. The following abbreviations are used in NMR spectra descriptions: s=singlet, d=doublet, t=triplet, q=quartet, m=multiplet, br=broad. IUPAC nomenclature is used for atom numbering. Purities of all synthesized compounds were confirmed by LC-MS analysis performed with a Shimadzu HPLC instrument with PE SCIEX API 150EX mass- and Shimadzu UV-(254 and 215 nm) detectors. Separation was achieved with a XBridge C18 3.5μ (4.6*100 mm) column with use of a gradient (5-95%) of acetonitrile in water both with 0.05% TFA over 10 min at 0.9 mLmin$^{-1}$.

Compound 2. Compound 1 (27.1 g, 141 mmol) was dissolved in toluene (100 mL). DMF-DMA (17.6 g, 148.0 mmol) was added and the reaction mixture was stirred at 70° C. When the starting material was consumed (monitored by TLC), the reaction mixture was allowed to cool to room temperature, and the solvent was evaporated to furnish 34.1 g (87%) of the title compound 2 (>95% pure) which was used in the next step.

Compound 3. Compound 2 (34.0 g, 138 mmol) and hydroxylamine hydrochloride (10.1 g, 145 mmol) were dissolved in MeOH (150 mL) and the resulting solution was stirred at room temperature. The reaction was monitored by HPLC. After 18 h, 90% of the solvent was evaporated and the residue was dissolved in CH2Cl2, washed with water and dried (Na$_2$SO$_4$). The solvent was evaporated to furnish 28.5 g (yield 84%) (>95% pure) of the compound 3.

Compound 4. Compound 3 (28.5 g, 115 mmol) was dissolved in 100 mL of dry THF and added to the suspension of LiAlH$_4$ (4.4 g, 115 mmol) in dry THF (200 ml) at a rate that maintains the reaction temperature at −20-5° C. The mixture was stirred at 0° C. for 1 h. The mixture was cooled to −15° C. and 9 ml saturated solution of potassium tartrate in was added at a rate that maintains the temperature under 10° C. After complete addition the mixture was stirred for 12 h at room temperature. The precipitate was collected by filtration, washed with THF. Concentration of the filtrate afforded compound 4 (20.3 g, 86%).

Compound 5. A 1-L Erlenmeyer flask, fitted with a magnetic stirrer, was charged with compound 4 (20.0 g, 97 mmol) and 400 ml of dry CH$_2$Cl$_2$. Activated MnO$_2$ (59.3 g, 682 mmol, 7 eq.) was slowly added. After a complete addition, a reflux condenser was attached to the reaction vessel, and the mixture was stirred at 40° C. for 20 h until acceptable conversion by NMR. The reaction was cooled, filtered through Celite™, and the residue was extracted several times with warm $CH_2Cl_2$. The combined extracts were evaporated to give compound 5 (15.5 g, 78%).

T813-0242 1-(4-((5-(3-Methoxyphenyl)isoxazol-4-yl)methyl)piperazin-1-yl)ethanone. The mixture of compound 5 (0.500 g, 2.46 mmol) and compound 6 (0.347 g, 2.71 mmol) in 10 mL of dichloromethane was stirred at RT for 1 h, then sodium triacetoxyborohydride (1.304 g, 6.15 mmol) was added and the mixture was stirred at RT overnight. The mixture was diluted with dichloromethane, washed with 10% aqueous solution of sodium carbonate, water and brine, dried over anhydrous $Na_2SO_4$, filtered and concentrated under reduced pressure. The obtained residue was separated by chromatography on silica gel to give T813-0242 (0.630 g, 81%). $^1H$ NMR (400 MHz, DMSO-$d_6$) δ ppm: 8.62; (s, 1H), 7.40-7.51; (m, 3H), 7.10; (m, 1H), 3.83; (s, 3H), 3.50; (s, 2H), 3.42; (m, 4H), 2.42; (dt, J=23.84, 4.52 Hz, 4H), 1.98; (s, 3H). LCMS m/z 316.3; $(M+H)^+$ Rt 4.01 min.

Additional derivatives of these compounds can be synthesized by standard techniques in the art, for example, see Modern Organic Synthesis in the Laboratory, Oxford University Press, USA (Sep. 10, 2007), and Advanced Organic Chemistry: Reactions, Mechanisms and Structure, Jerry March, John Wiley & Sons, New York (1992), which are hereby incorporated by reference.

Results and Discussion

A cell-based small molecule screening with 50,024 compounds was performed based on AML cell lines that grow in a PAK1-dependent manner, which has been previously described (Pandolfi et al., 2015). This was followed by single point PAK1 enzymatic activity screening against 360 compounds. Forty-six identified compounds that scored positive in this assay were subjected to enzymatic activity assays against other PAK family kinases including PAK2, PAK3, PAK4, PAK6, and PAK7. Compounds that were highly selective for PAK1 and showed less than 30% inhibitory activity towards all other family members were selected for further testing and subjected to an additional round of PAK1 enzymatic testing by concentration response curves (FIG. 1). This is resulted in the identification of lead scaffold compounds (FIG. 2). Those compounds were studied in further detail and key biochemical, pharmacokinetic, and structure-activity characteristics were determined.

C273 series: Compound C273-0489 showed an IC50 of 470 nM against PAK1, but no significant inhibitory activity against any of the other PAK family members (Table 1). Also, there was no significant inhibition against a larger kinase panel (FIG. 3); thus series C273 compounds appear to be highly selective for inhibiting PAK1.

TABLE 1

Selectivity of Compound C273-0489 inhibition for PAK1 versus related PAK kinases.

| DiscoveRx Gene Symbol | Entrez Gene Symbol | C273-0489 |
|---|---|---|
| PAK2 | PAK2 | 95 |
| PAK3 | PAK3 | 100 |
| PAK4 | PAK4 | 100 |
| PAK6 | PAK6 | 100 |
| PAK7 | PAK7 | 72 |

Figure 4:
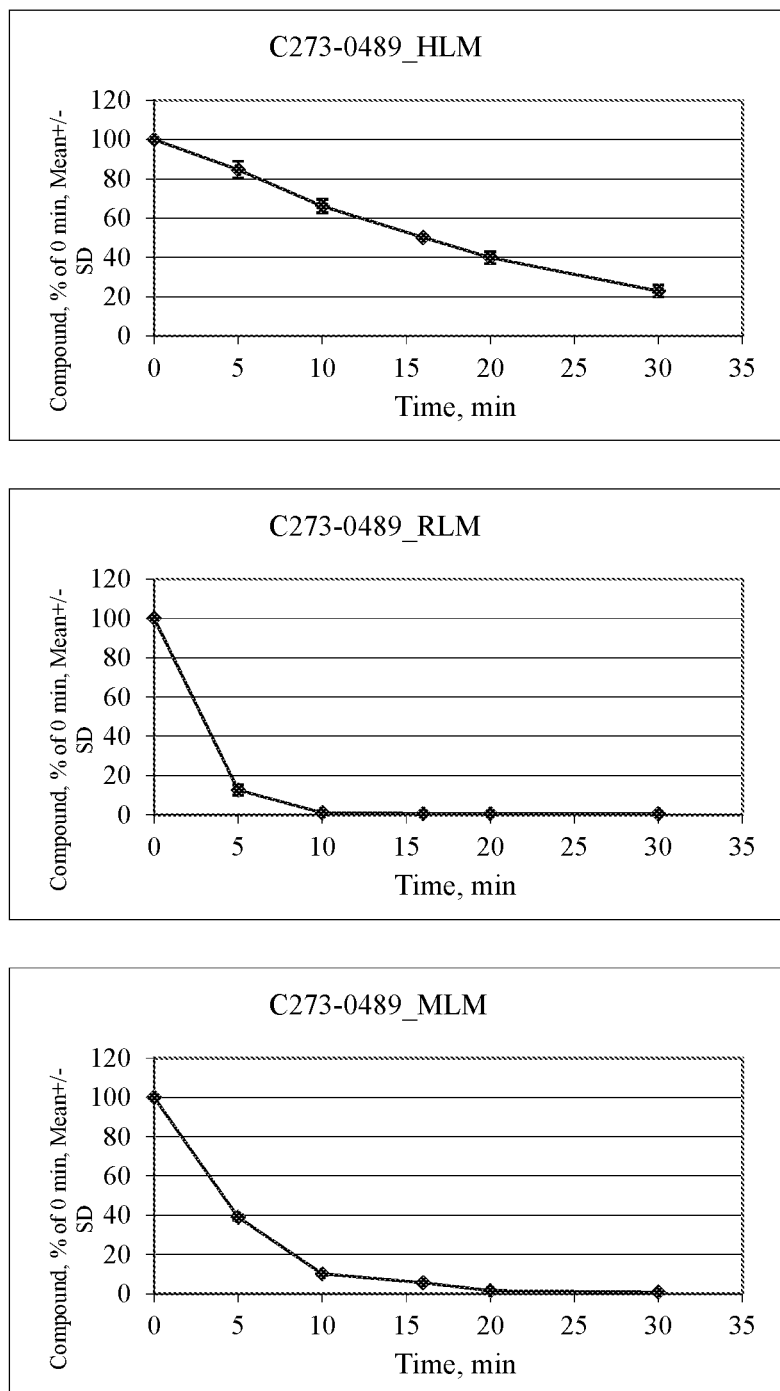
FIG. 4. Microsomal stability assessment for Compound C273-0489. HLM—human, RLM—rat, MLM—mouse.
Figures 5A, 5B:
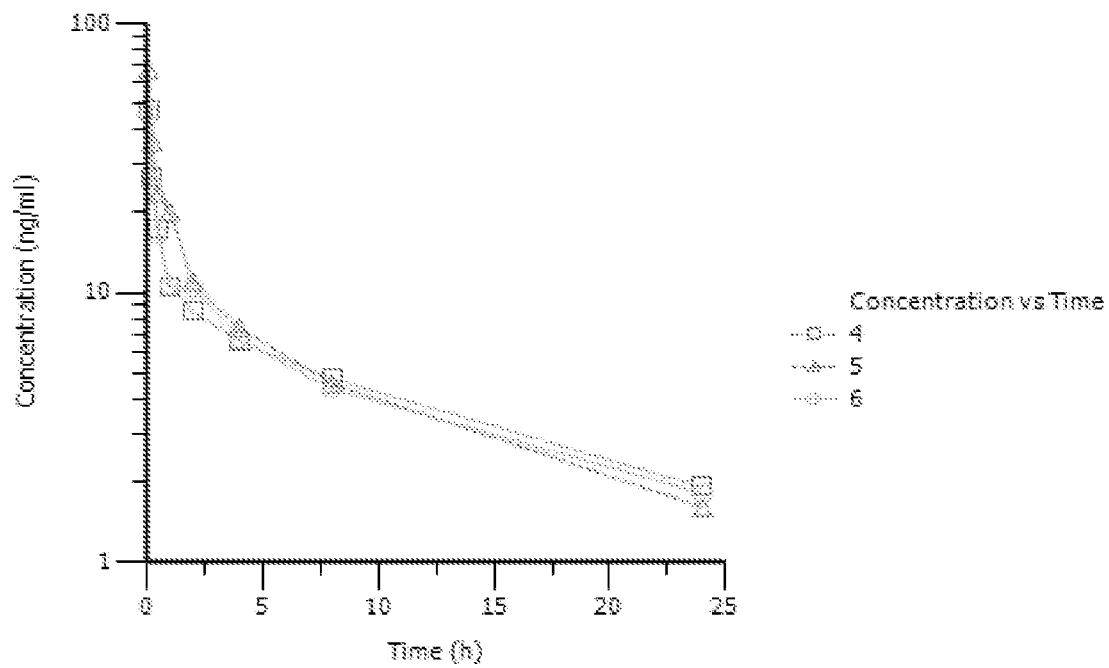
FIG. 5A-5B. Pharmacokinetic (PK) assessment of Compound C273-0489 performed in rats. A. Plasma concentration after 2 mg/kg IV injection. B. Plasma concentrations after 2 mg/kg IV injection and after 10 mg/kg PO administration.

Microsomal stability assays were performed (human, rat, and mouse) for Compound C273-0489 and are summarized in FIG. 4 and Table 2. Pharmacokinetic (PK) assessment was performed in rats after 2 mg/kg C273-0489 IV injection, and after 10 mg/kg C273-0489 PO administration (FIG. 5 and Table 3). In summary, the data show that series C273 has multiple active derivatives, favorable structure-activity relationship (SAR), low molecular weight (which will enable addition of substituents for further optimization), and favorable initial PK properties.

TABLE 2

Microsomal stability assessment of Compound C273-0489.

| Microsomes | t½, min | CLint | CLint, hep | CLh | ER |
|---|---|---|---|---|---|
| Human | 13.94 | 0.1988 | 229.9122 | 19.24 | 0.89 |
| Rat | 1.51 | 1.8308 | 3295.44 | 54.10 | 0.98 |
| Mouse | 4.18 | 0.6636 | 2612.925 | 87.00 | 0.97 |

TABLE 3

Pharmacokinetic (PK) assessment of Compound C273-0489 performed in rats after 2 mg/kg IV injection, and after 10 mg/kg PO administration.

| | IV, 2 mg/kg | | | | | |
|---|---|---|---|---|---|---|
| | Parameter | | | | | |
| Units | AUCINF h*ng/ml | AUClast h*ng/ml | C0 ng/ml | Cl ml/min/kg | Cmax ng/ml | T ½ h |
| Mean | 156.11 | 128.94 | 71.71 | 213.75 | 53.37 | 10.60 |
| | PO, 10 mg/kg | | | | | |
| | Parameter | | | | | |
| Units | AUCINF h*ng/ml | AUClast h*ng/ml | Cl/F ml/min/kg | Cmax ng/ml | T ½ h | |
| Mean | #DIV/0! | 92.68 | #DIV/0! | 17.40 | #DIV/0! | |
| | IV, 2 mg/kg | | | | | |
| | Parameter | | | | | |
| Units | K el 1/h | MRTINF h | MRTlast h | Tmax h | Vss l/kg | Vz l/kg |
| Mean | 0.07 | 12.27 | 6.51 | 0.08 | 157.86 | 196.56 |
| | PO, 10 mg/kg | | | | | |
| | Parameter | | | | | |
| Units | K el 1/h | MRTINF h | MRTlast h | Tmax h | Vz/F ml/kg | |
| Mean | #DIV/0! | #DIV/0! | 3.97 | 3.33 | #DIV/0! | |

T813 series: Compound T813-0242 showed an IC50 of 900 nM against PAK1, but no significant inhibitory activity against any of the other PAK family members (Table 4). Also, there was no significant inhibition against a larger kinase panel (FIG. 6). Thus, series T813 seems to be highly selective for inhibiting PAK1.

Compound T813-0242

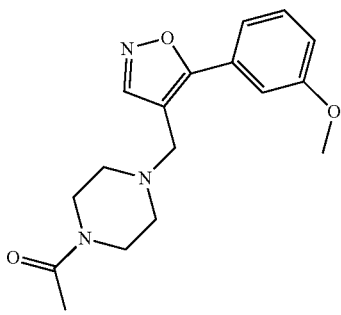

TABLE 4

Selectivity of Compound T813-0242 inhibition for PAK1 versus related PAK kinases.

| DiscoveRx Gene Symbol | Entrez Gene Symbol | T813-0242 |
|---|---|---|
| PAK2 | PAK2 | 100 |
| PAK3 | PAK3 | 100 |
| PAK4 | PAK4 | 100 |
| PAK6 | PAK6 | 95 |
| PAK7 | PAK7 | 98 |

Figure 7:
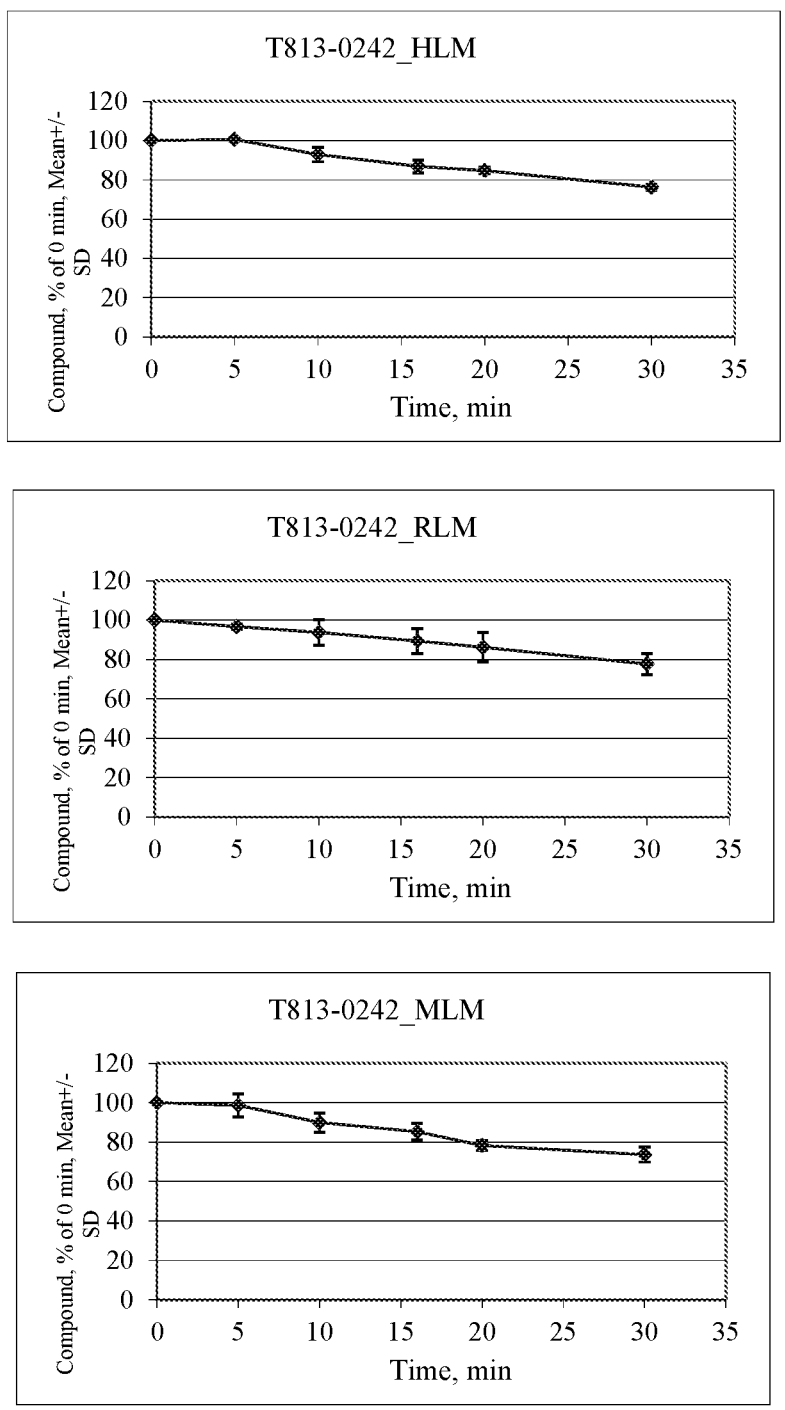
FIG. 7. Microsomal stability assessment for Compound T813-0242. HLM—human, RLM—rat, MLM—mouse.
Figure 8A:
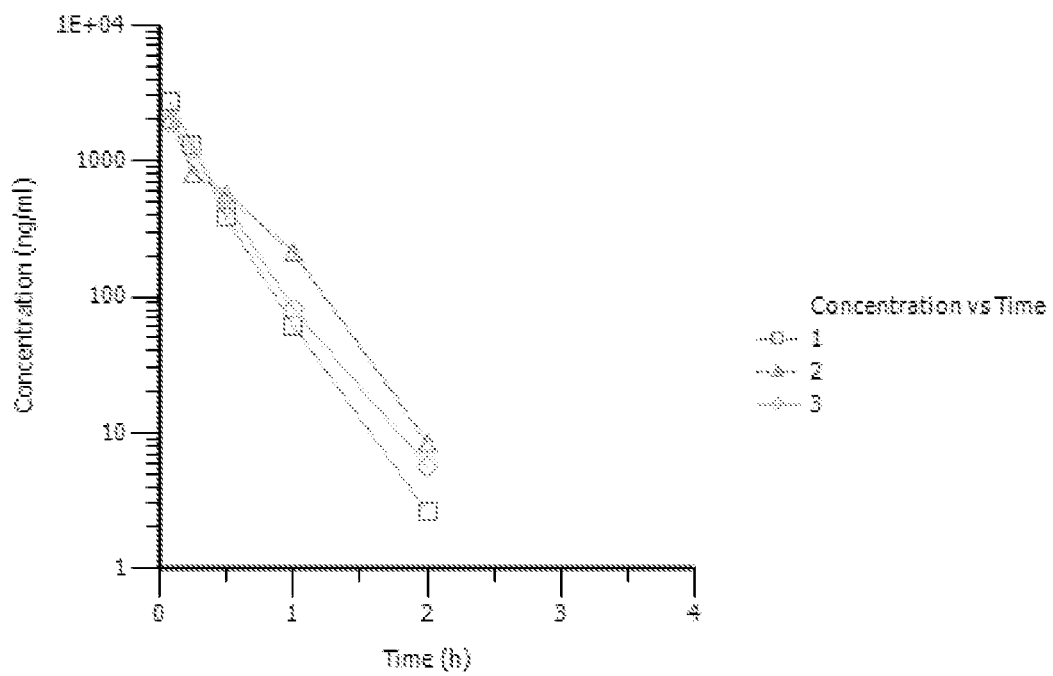
FIG. 8A-8B. Pharmacokinetic (PK) assessment of Compound T813-0242 performed in rats. A. Plasma concentration after 2 mg/kg IV injection. B. Plasma concentrations after 10 mg/kg PO administration.
Figure 8B:
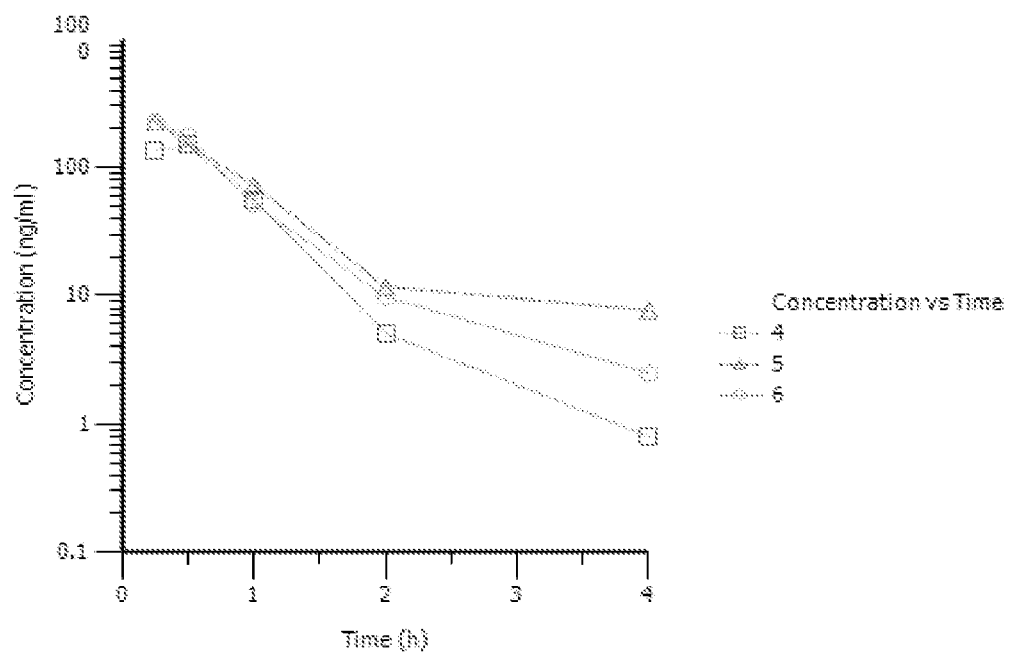

Microsomal stability assays were performed (human, rat, and mouse) and are shown in FIG. 7 and Table 5. PK assessment was performed in rats after 2 mg/kg IV injection, and 10 mg/kg PO administration (FIG. 8 and Table 6). In summary, the data show that series T813 has low molecular weight (which will enable addition of substituents for further optimization), high specificity for PAK1, and favorable biochemical and PK properties.

TABLE 5

Microsomal stability assessment of Compound T813-0242.

| Microsomes | t½, min | CLint | CLint, hep | CLh | ER |
|---|---|---|---|---|---|
| Human | 71.44 | 0.0388 | 44.8722 | 14.31 | 0.66 |
| Rat | 81.53 | 0.034 | 61.2 | 28.97 | 0.53 |
| Mouse | 62.43 | 0.0444 | 174.825 | 59.41 | 0.66 |

TABLE 6

Pharmacokinetic (PK) assessment of Compound T813-0242 performed in rats after 2 mg/kg IV injection, and after 10 mg/kg PO administration.

| | PO plasma | | IV plasma | | |
|---|---|---|---|---|---|
| | | Dose, mg/kg | | Dose, mg/kg | Fabs, % |
| AUClast | | | | | |
| | 171.0 | 10 | 909 | 2 | 3.8% |
| AUCINF | | | | | |
| | 175 | 10 | 911 | 2 | 3.8% |

TABLE 6-continued

Pharmacokinetic (PK) assessment of Compound T813-0242 performed in rats after 2 mg/kg IV injection, and after 10 mg/kg PO administration.

IV, 2 mg/kg

| | Parameter | | | | | |
|---|---|---|---|---|---|---|
| Units | AUCINF h*ng/ml | AUClast h*ng/ml | C0 ng/ml | Cl ml/min/kg | Cmax ng/ml | T ½ h |
| Mean | 910.60 | 908.70 | 3153.95 | 36.74 | 2209.17 | 0.23 |

PO, 10 mg/kg

| | Parameter | | | | |
|---|---|---|---|---|---|
| Units | AUCINF h*ng/ml | AUClast h*ng/ml | Cl/F ml/min/kg | Cmax ng/ml | T ½ h |
| Mean | 175.12 | 170.98 | 973.87 | 201.67 | 0.69 |

IV, 2 mg/kg

| | Parameter | | | | | |
|---|---|---|---|---|---|---|
| Units | K el 1/h | MRTINF h | MRTlast h | Tmax h | Vss l/kg | Vz l/kg |
| Mean | 3.03 | 0.30 | 0.29 | 0.08 | 0.65 | 0.73 |

PO, 10 mg/kg

| | Parameter | | | | |
|---|---|---|---|---|---|
| Units | K el 1/h | MRTINF h | MRTlast h | Tmax h | Vz/F l/kg |
| Mean | 1.05 | 0.84 | 0.75 | 0.33 | 56.24 |

D245 series: Compound D245-0091 showed an IC50 of 5 µM against PAK1, but no significant inhibitory activity against any of the other PAK family members (Table 7). Also, there was no significant inhibition against a larger kinase panel (FIG. 9). Thus series D245 appears to be highly selective for inhibiting PAK1.

Compound D245-0091

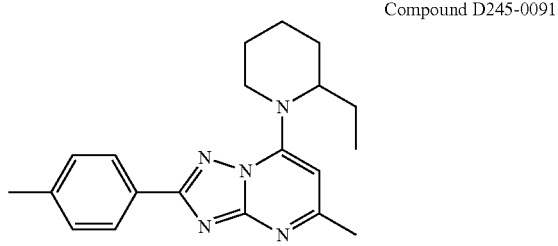 [SMILES: CCC1CCCCN1c1cc(C)nc2nc(-c3ccc(C)cc3)nn12]

TABLE 7

Selectivity of Compound D245-0091 inhibition for PAK1 versus related PAK kinases.

| DiscoveRx Gene Symbol | Entrez Gene Symbol | D245-0091 |
|---|---|---|
| PAK2 | PAK2 | 89 |
| PAK3 | PAK3 | 100 |
| PAK4 | PAK4 | 95 |
| PAK6 | PAK6 | 89 |
| PAK7 | PAK7 | 89 |

Figure 10:
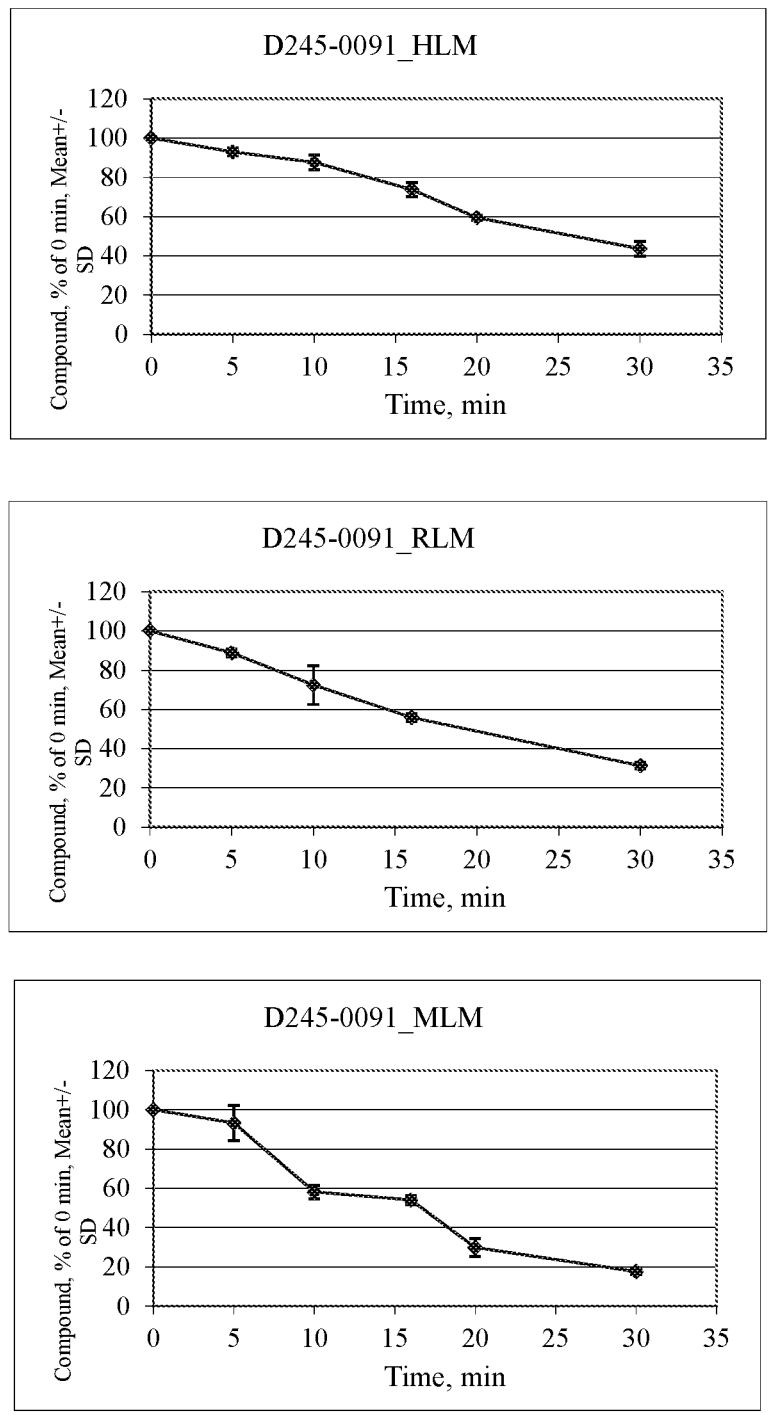
FIG. 10. Microsomal stability assessment for Compound D245-0091. HLM—human, RLM—rat, MLM—mouse.
Figure 11A:
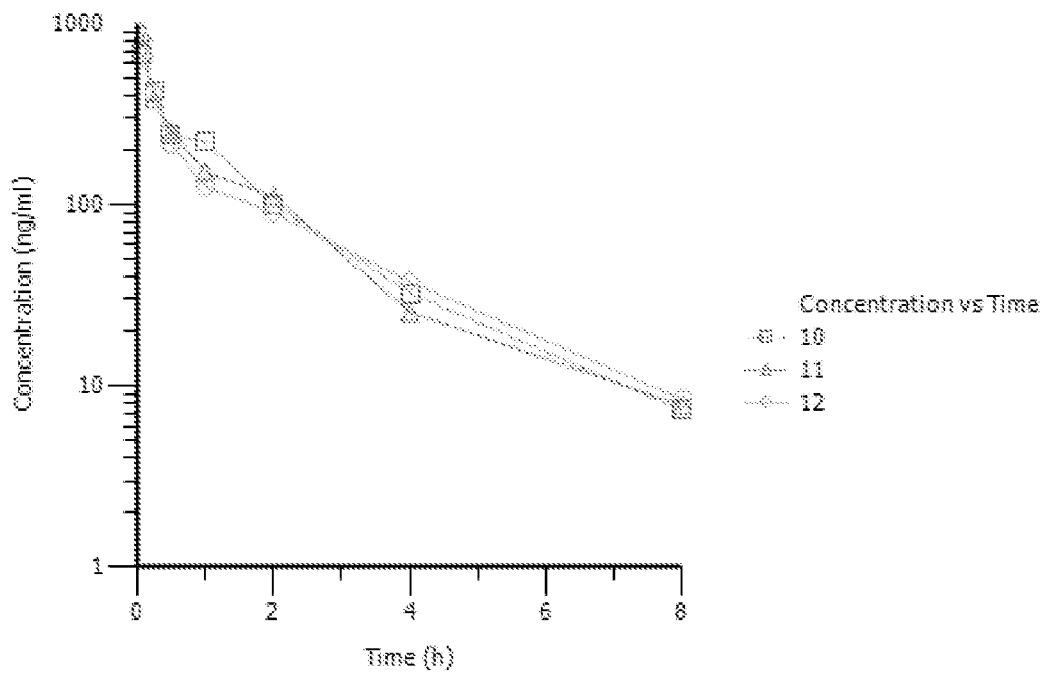
FIG. 11A-11B. Pharmacokinetic (PK) assessment of Compound D245-0091 performed in rats. A. Plasma concentration after 2 mg/kg IV injection. B. Plasma concentrations after 10 mg/kg PO administration.
Figure 11B:
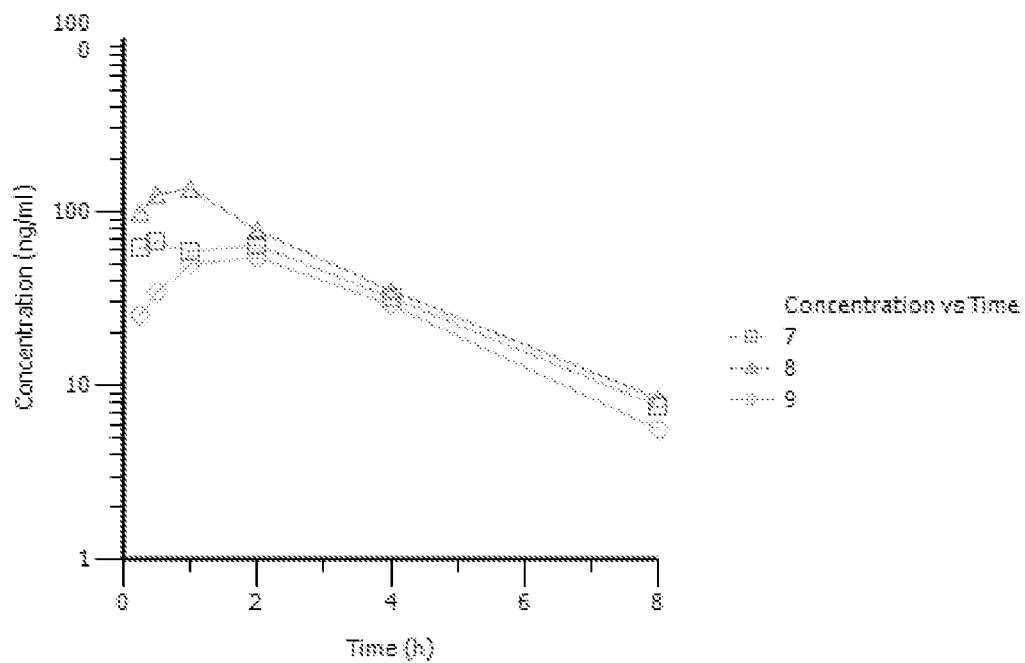

Microsomal stability assays were performed (human, rat, and mouse) and are shown in FIG. 10 and Table 8. PK assessment was performed in rats after 2 mg/kg IV injection, and 10 mg/kg PO administration (FIG. 11 and Table 9). In summary, the data show that series D245 has low molecular weight (which will enable addition of substituents for further optimization) and high specificity for PAK1.

TABLE 8

Microsomal stability assessment of Compound D245-0091.

| Microsomes | t½, min | CLint | CLint, hep | CLh | ER |
|---|---|---|---|---|---|
| Human | 24.32 | 0.114 | 131.841 | 18.11 | 0.83 |
| Rat | 17.41 | 0.1592 | 286.56 | 46.14 | 0.84 |
| Mouse | 11.40 | 0.2432 | 957.6 | 82.27 | 0.91 |

TABLE 9

Pharmacokinetic (PK) assessment of Compound D245-0091 performed in rats after 2 mg/kg IV injection, and after 10 mg/kg PO administration.

| PO plasma | | IV plasma | | |
|---|---|---|---|---|
| Dose, mg/kg | | Dose, mg/kg | | Fabs, % |
| AUClast | | | | |
| 315.0 | 10 | 695 | 2 | 9.1% |
| AUCINF | | | | |
| 334 | 10 | 714 | 2 | 9.4% |

IV, 2 mg/kg

| | Parameter | | | | | |
|---|---|---|---|---|---|---|
| Units | AUCINF h*ng/ml | AUClast h*ng/ml | C0 ng/ml | Cl ml/min/kg | Cmax ng/ml | T ½ h |
| Mean | 713.53 | 694.74 | 1013.08 | 46.84 | 739.83 | 1.66 |

PO, 10 mg/kg

| | Parameter | | | | |
|---|---|---|---|---|---|
| Units | AUCINF h*ng/ml | AUClast h*ng/ml | Cl/F ml/min/kg | Cmax ng/ml | T ½ h |
| Mean | 334.07 | 314.54 | 524.81 | 85.67 | 1.87 |

IV, 2 mg/kg

| | Parameter | | | | |
|---|---|---|---|---|---|
| Units | K el 1/h | MRTINF h | MRTlast h | Tmax h | Vss l/kg | Vz l/kg |
| Mean | 0.42 | 1.69 | 1.46 | 0.08 | 4.77 | 6.74 |

PO, 10 mg/kg

| | Parameter | | | | |
|---|---|---|---|---|---|
| Units | K el 1/h | MRTINF h | MRTlast h | Tmax h | Vz/F l/kg |
| Mean | 0.37 | 3.01 | 2.52 | 1.17 | 84.84 |

42-0125_1 series: Three active compounds were identified in the screen, which had been previously reported in the literature. Their structures are shown below:

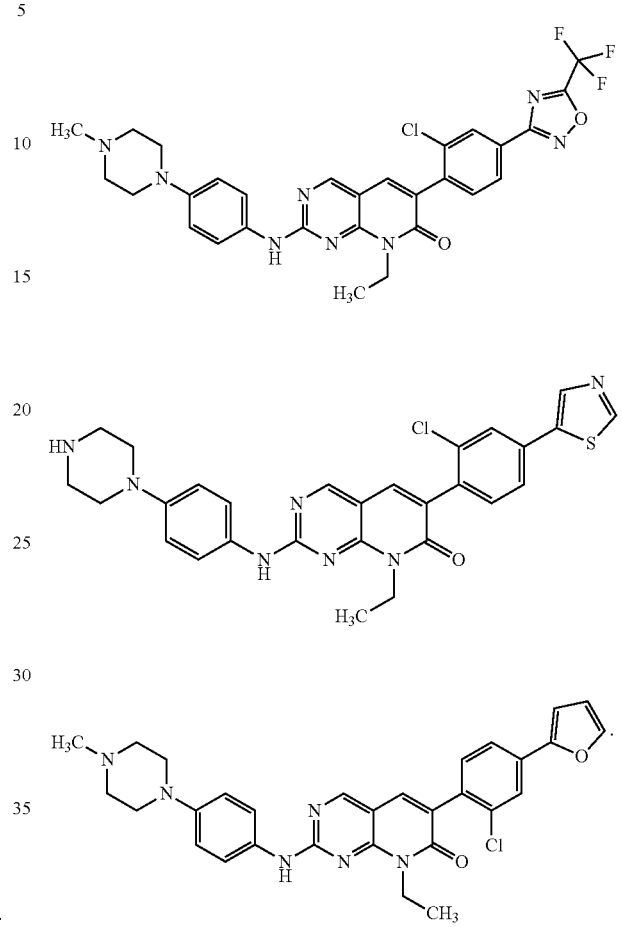

Structure-activity relationship analysis showed that the left side of the molecule is critical of selectivity. Optimization of the biaryl moiety led to the design and preparation of novel molecule, 42-0125_1:

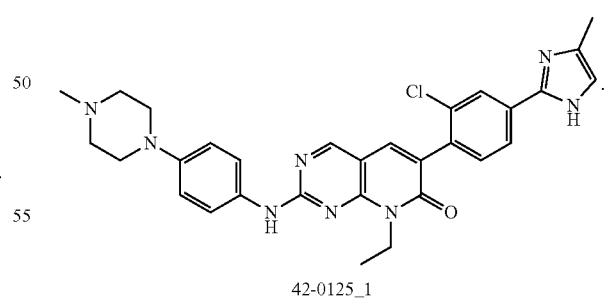

42-0125_1

Figure 12:
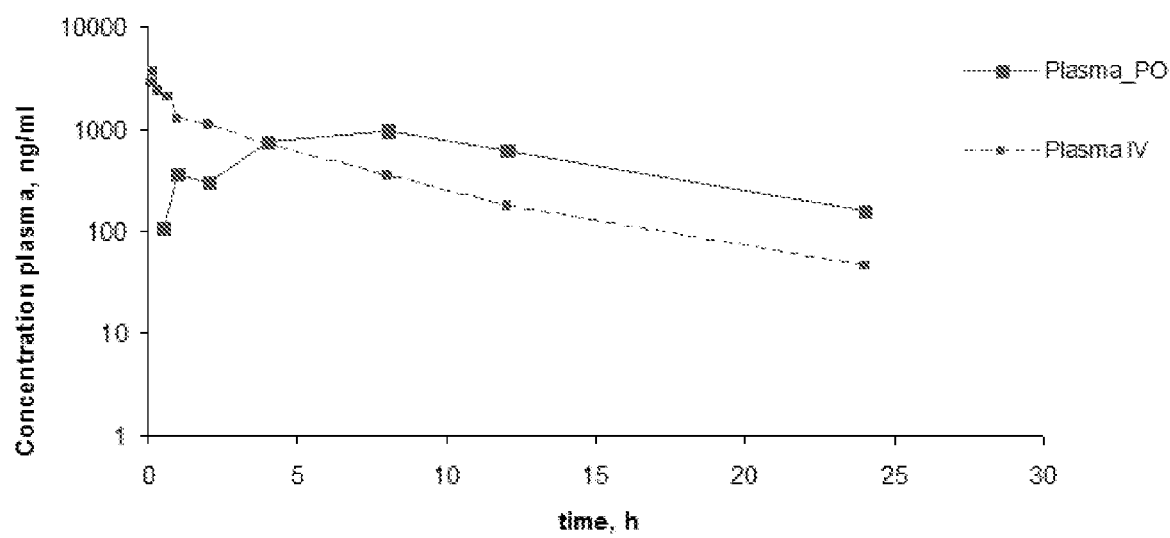
FIG. 12. Pharmacokinetic (PK) assessment of Compound 42-0125_1 performed in rats. Plasma concentration after 3 mg/kg IV injection and after 30 mg/kg PO administration.

Compound 42-0125_1 showed an IC50 of <30 nM against PAK1. Assessment of this novel compound for microsomal stability (Table 10), solubility (Table 11), CYP inhibition (Table 12), and caco-2 permeability (Table 13) properties revealed favorable characteristics. Pharmacokinetic properties were determined in rats upon IV (3 mg/kg) and PO (30 mg/kg) application (FIG. 12 and Table 14).

TABLE 10

Microsomal stability assessment of Compound 42-0125_1.
Microsomal Stability

| | t½, min | Clint, µl/min/mg protein |
|---|---|---|
| HLM | 119 | 12 |
| RLM | 147 | 9 |

TABLE 11

Solubility assessment of Compound 42-0125_1.
Solubility

| IDNUMBER | Solubility in SGF, 1% DMSO, µM | Solubility in UB pH 2, 1% DMSO, µM | Solubility in UB pH 7, 1% DMSO, µM |
|---|---|---|---|
| 42-0125_1 | 58 | 59 | 25 |

TABLE 12

CYP inhibition assessment of Compound 42-0125_1.
CYP inhibition

| 1A2-Phenacetine | >1E−05 |
| 2C19-Mephenytoin | 5.6E−06 |
| 3A4-Midazolam | 8.9E−06 |
| 3A4-Testosterone | >1E−05 |
| 2D6-Dextromethorphan | >1E−05 |
| 2C9-Tolbutamide | 7.2E−06 |
| 2C8-Amodiaquine | >1E−05 |

TABLE 13

Caco-2 permeability assessment of Compound 42-0125_1.
Caco-2

| ID | Papp A-B, 10-6 cm/s | SD (A-B) | Papp B-A, 10-6 cm/s | SD(B-A) | Assym index |
|---|---|---|---|---|---|
| 42-0125_1 | 3.9 | 0.6 | 3.8 | 0.5 | 1.0 |

TABLE 14

Pharmacokinetic (PK) assessment of Compound 42-0125_1 performed in rats after 3 mg/kg IV injection, and after 30 mg/kg PO administration

| Admin | Dose mg/kg | Tmax h | Cmax ng/ml | AUC0→t AUC last ng*h/ml | AUC0→∞ AUC INF_obs ng*h/ml | T ½ HL_Lambda_z h | Cl_obs ml/h/kg | Vss_obs ml/kg | MRT MRT last h | Biovailability % |
|---|---|---|---|---|---|---|---|---|---|---|
| IV | 3 | 0.17 | 3624 | 9753 | 10055 | 5 | 298 | 1705 | 5 | |
| PO | 30 | 8 | 943 | 12616 | 14020 | 6.19 | | | 10 | 13.9% |

REFERENCES

Allen, J. D., Lints, T., Jenkins, N. A., Copeland, N. G., Strasser, A., Harvey, R. P. and Adams, J. M. (1991). Novel murine homeo box gene on chromosome 1 expressed in specific hematopoietic lineages and during embryogenesis. Genes Dev. 4, 509-520.

Deguchi, Y. and Kehrl, J. H. (1991). Selective expression of two homeobox genes in CD34-positive cells from human bone marrow. Blood 2, 323-328.

Deguchi, Y., Kirschenbaum, A. and Kehrl, J. H. (1992). A diverged homeobox gene is involved in the proliferation and lineage commitment of human hematopoietic progenitors and highly expressed in acute myelogenous leukemia. Blood 11, 2841-2848.

Hanahan D, Weinberg R A: The hallmarks of cancer. Cell 2000, 100(1):57-70.

Hentsch, B., Lyons, I., Li, R., Hartley, L., Lints, T. J., Adams, J. M. and Harvey, R. P. (1996). Hlx homeo box gene is essential for an inductive tissue interaction that drives expansion of embryonic liver and gut. Genes Dev. 1, 70-79.

Marcucci, G., Haferlach, T. and Dohner, H. (2011). Molecular genetics of adult acute myeloid leukemia: prognostic and therapeutic implications. J. Clin. Oncol. 5, 475-486.

Pandolfi A, Stanley R F, Yu Y, Bartholdy B, Pendurti G, Gritsman K, Boultwood J, Chernoff J, Verma A, Steidl U. (2015). PAK1 is a therapeutic target in acute myeloid leukemia and myelodysplastic syndrome. Blood 27; 126 (9):1118-27. Epub 2015 Jul. 13.

Steidl, U., Rosenbauer, F., Verhaak, R. G., Gu, X., Ebralidze, A., Otu, H. H., Klippel, S., Steidl, C., Bruns, I., Costa, D. B. et al. (2006). Essential role of Jun family transcription factors in PU.1 knockdown-induced leukemic stem cells. Nat. Genet. 11, 1269-1277.

U.S. Patent Application Publication No. 2015/0299336 A1, published Oct. 22, 2015, Steidl, Therapeutic and diagnostic target gene in acute myeloid leukemia.

U.S. Patent Application Publication No. 2015/0359815 A1, published Dec. 15, 2015, Steidl, et al., PAK1 inhibition for treatment of acute myeloid leukemia and myelodysplastic syndromes.

What is claimed is:

1. A method of treating acute myeloid leukemia (AML) or myelodysplastic syndrome (MDS) in a subject, the method comprising administering to the subject a compound of Formula I, II, III or IV in an amount effective to inhibit p21 protein (Cdc42/Rac)-activated kinase (PAK1) in a subject, wherein Formula I has the structure:

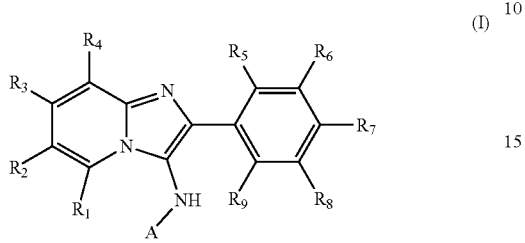

wherein $R_1$, $R_2$, $R_3$ and $R_4$ of Formula I are independently H, halogen, —OH, —NH$_2$, C1-C6 alkyl, —OCH$_3$, —COCH$_3$, 5- or 6-membered cyclic or heterocyclic, 5- or 6-membered aryl or heteroaryl, wherein the heteroaryl or heterocyclic contains one or more of the same or different heteroatom, or optionally substituted phenyl or benzyl, wherein the phenyl or benzyl is optionally substituted with one or more of halogen, —OH, —NH$_2$, —CH$_3$, or —OCH$_3$;

wherein $R_5$, $R_6$, $R_7$, $R_8$ and $R_9$ of Formula I are independently H, halogen, —OH, —NH$_2$, —NHCH$_3$, —N(CH$_3$)$_2$, C1-C6 alkyl, —OCH$_3$, —SH, —OCH$_3$, —SCH$_3$, 5- or 6-membered cyclic or heterocyclic, or 5- or 6-membered aryl or heteroaryl, wherein the heteroaryl or heterocyclic contains one or more of the same or different heteroatom, or optionally substituted phenyl or benzyl, wherein the phenyl or benzyl is optionally substituted with one or more of halogen, —OH, —NH$_2$, —CH$_3$, or —OCH$_3$;

wherein A is a heteroaryl or heterocyclic containing one or more of the same or different heteroatom, or

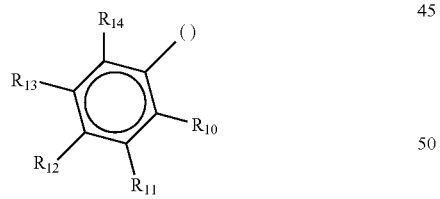

where ( ) represents the point of attachment to the molecular scaffold;

wherein $R_{10}$, $R_{11}$, $R_{12}$, $R_{13}$ and $R_{14}$ of Formula I are independently H, halogen, —OH, —NH$_2$, C1-C6 alkyl, —OCH$_3$, —COCH$_3$, 5- or 6-membered cyclic or heterocyclic, or 5- or 6-membered aryl or heteroaryl, wherein the heteroaryl or heterocyclic contains one or more of the same or different heteroatom, and/or $R_{10}$ and $R_{11}$, or $R_{11}$ and $R_{12}$, or $R_{12}$ and $R_{13}$, or $R_{13}$ and $R_{14}$ of Formula I together form a 5- or 6-membered hetrocyclic or heteroaryl containing one or more of the same or different heteroatom;

or a pharmaceutically acceptable salt thereof;

wherein Formula II has the structure:

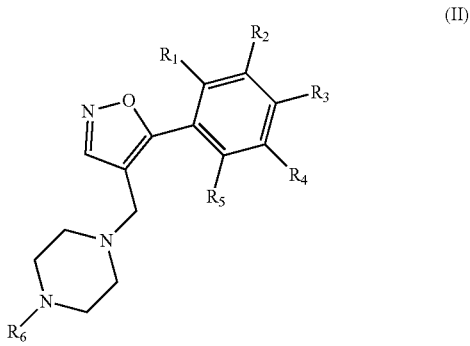

wherein $R_1$, $R_2$, $R_3$, $R_4$, $R_5$ and $R_6$ of Formula II are independently H, halogen, —OH, —NH$_2$, —NHCH$_3$, —N(CH$_3$)$_2$, C1-C6 alkyl, —OCH$_3$, —COCH$_3$, —SH, or —SCH$_3$, or a pharmaceutically acceptable salt thereof;

wherein Formula III has the structure:

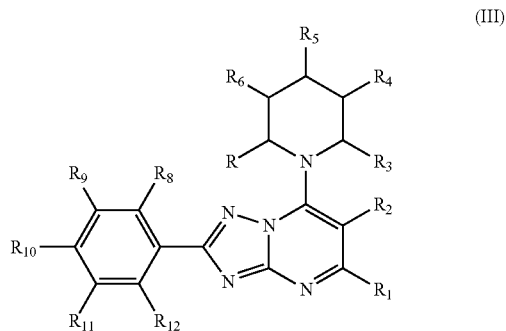

wherein $R_1$, $R_2$, $R_3$, $R_4$, $R_5$, $R_6$, $R_7$, $R_8$, $R_9$, $R_{10}$, $R_{11}$ and $R_{12}$ of Formula III are independently H, halogen, —OH, —NH$_2$, —NHCH$_3$, —N(CH$_3$)$_2$, C1-C6 alkyl, —OCH$_3$, —COCH$_3$, —SH, or —SCH$_3$, or a pharmaceutically acceptable salt thereof; and wherein Formula IV has the structure:

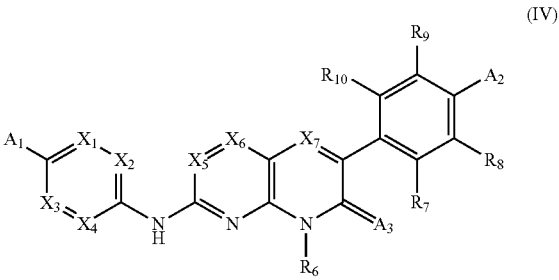

wherein A1 and A2 of Formula IV are independently

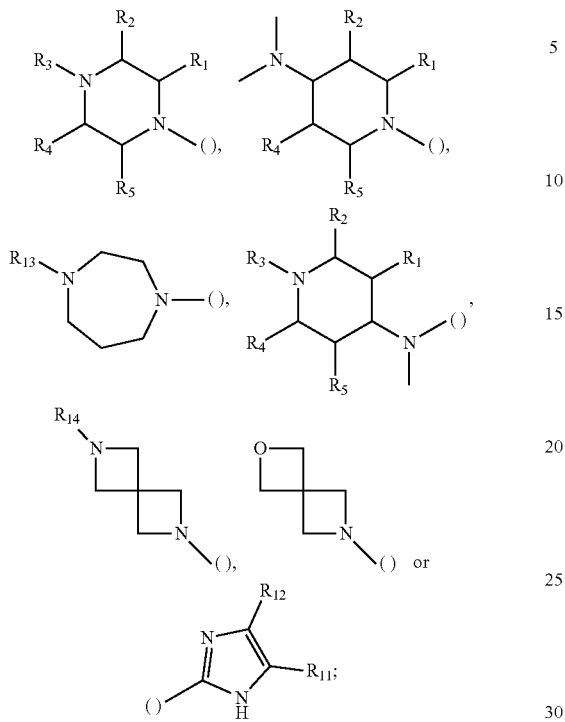

where ( ) represents the point of attachment to the molecular scaffold;

wherein $X_1$, $X_2$, $X_3$, $X_4$, $X_5$ and $X_7$ of Formula IV are independently CH or N;

wherein $X_6$ of Formula IV is CH, N or

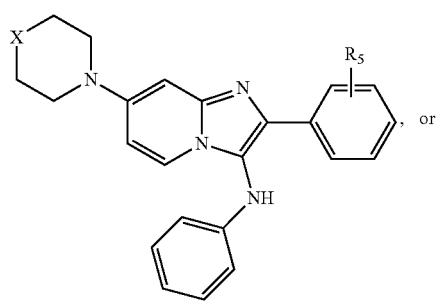

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$ and $R_{16}$ of Formula IV are independently H, halogen, —OH, —$NH_2$, —$NHCH_3$, —$N(CH_3)_2$, C1-C6 alkyl, —$OCH_3$, —$COCH_3$, —SH, or —$SCH_3$;

wherein A3 of Formula IV is O or N, and when A3 is N, $R_6$ is a C2 alkyl that bonds to the N of A3;

or a pharmaceutically acceptable salt thereof.

2. The method of claim 1, wherein one or both of $R_2$ and $R_6$ of Formula I is halogen.

3. The method of claim 1, wherein one or more of $R_1$, $R_4$, $R_{10}$ and $R_{14}$ of Formula I is —$CH_3$.

4. The method of claim 1, wherein $R_7$ of Formula I is —OH, —$OCH_3$, —$N(CH_3)_2$ or —$SCH_3$.

5. The method of claim 1, wherein $R_6$ or $R_7$ of Formula I is —$OCH_3$.

6. The method of claim 1, wherein A of Formula I is a pyridine, pyrimidine or pyrazine.

7. The method of claim 1, wherein the compound of Formula I has the formula

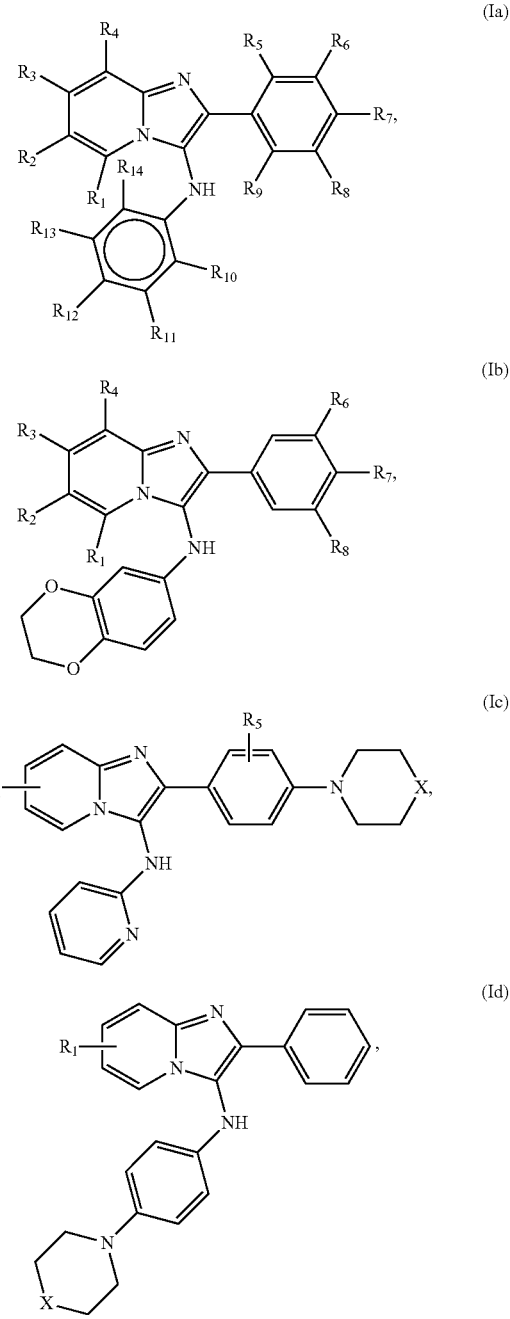

-continued (If)

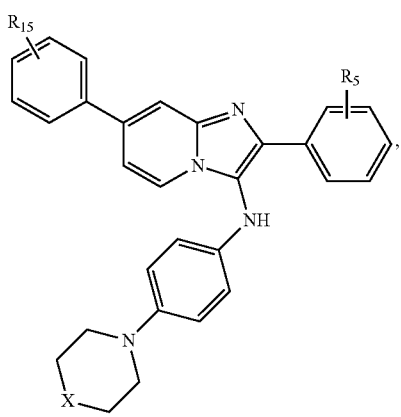

wherein R₁, R₂, R₃ and R₄ are independently H, halogen, —OH, —NH₂, —CH₃ or —OCH₃;

wherein R₅, R₆, R₇, R₈ and R₉ are independently H, halogen, —OH, —NH₂, —NHCH₃, —N(CH₃)₂, —CH₃, —OCH₃, —SH or —SCH₃, wherein R₁₀, R₁₁, R₁₂, R₁₃, R₁₄ and R₁₅ are independently H, halogen, —OH, —NH₂, —CH₃ or —OCH₃, wherein any X is independently CH₂, NH, O or S, or a pharmaceutically acceptable salt thereof.

8. The method of claim 1, wherein in the compound of Formula IV, X₁, X₂, X₃ and X₄ are CH; or X₁ is N, and X₂, X₃ and X₄ are CH; or X₂ is N, and X₁, X₃ and X₄ are CH; or X₁ and X₃ are N, and X₂ and X₄ are CH; or X₅ is N, and X₆ and X₇ are CH; or X₅ and X₇ are N, and X₆ is CH; or X₆ is N, and X₅ and X₇ are CH; or X₅ is N, X₇ is CH, and X₆ is

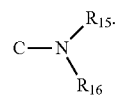

9. The method of claim 1, wherein the compound of Formula IV has the formula

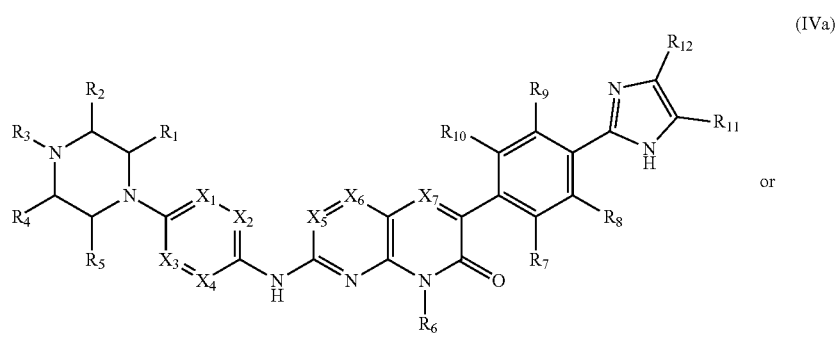

(IVa)

or

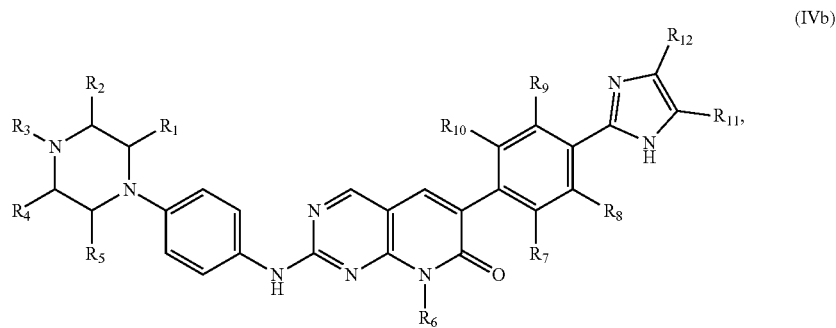

(IVb)

or a pharmaceutically acceptable salt thereof.

10. The method of claim 1, wherein any halogen is independently Br, Cl or I.

11. The method of claim 1, wherein any C1-C6 alkyl is independently —CH$_3$ or —CH$_2$CH$_3$.

12. The method of claim 1, wherein the compound of Formula I is selected from the group consisting of

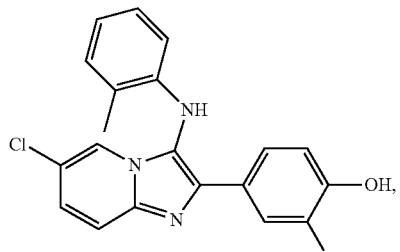

,

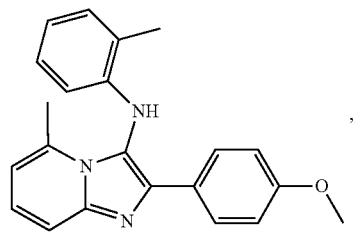

,

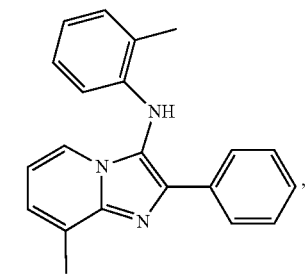

,

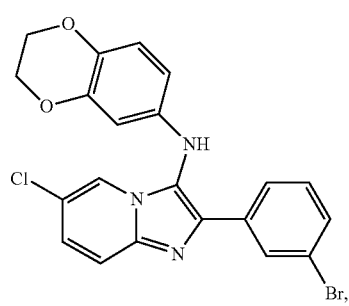

,

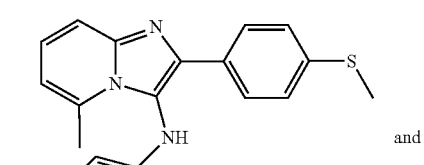 and

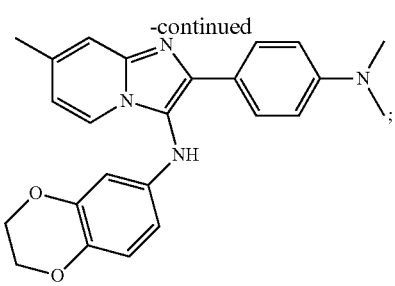

or a pharmaceutically acceptable salt thereof.

13. The method of claim 1, wherein the compound of Formula II has the structure

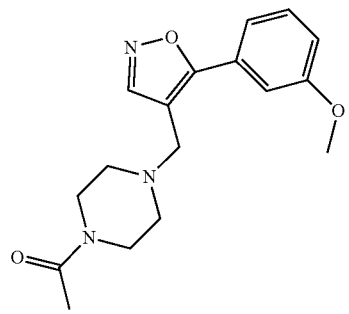 [SMILES: COc1cccc(-c2oncc2CN2CCN(C(C)=O)CC2)c1]

or a pharmaceutically acceptable salt thereof.

14. The method of claim 1, wherein the compound of Formula III has the structure

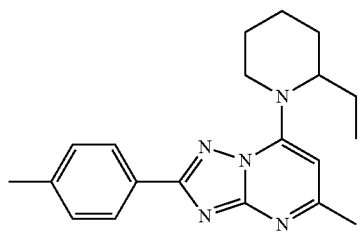 [SMILES: CCC1CCCCN1c1cc(C)nc2nc(-c3ccc(C)cc3)nn12]

or a pharmaceutically acceptable salt thereof.

15. The method of claim 1, wherein the compound of Formula IV has the structure

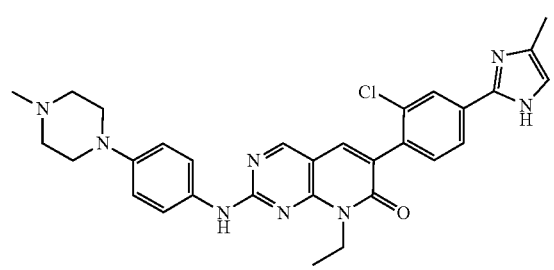 [SMILES: CCn1c(=O)c(-c2ccc(-c3nc(C)c[nH]3)cc2Cl)cc2cnc(Nc3ccc(N4CCN(C)CC4)cc3)nc21]

or a pharmaceutically acceptable salt thereof.

16. The method of claim 1, wherein the compound causes only 0-5% reduction in the activity of PAK2, PAK3, PAK4, PAK5, PAK6 or PAK7 at the same dose that is used to inhibit PAK1; or only 0-10% reduction in the activity of PAK2, PAK3, PAK4, PAK5, PAK6 or PAK7 at the same dose that is used to inhibit PAK1;

or 0-15% reduction in the activity of PAK2, PAK3, PAK4, PAK5, PAK6 or PAK7 at the same dose that is used to inhibit PAK1;

or 0-30% reduction in the activity of PAK2, PAK3, PAK4, PAK5, PAK6 or PAK7 at the same dose that is used to inhibit PAK1.

17. The method of claim 1, wherein the compound reduces proliferation of AML or MDS cells; and/or induces apoptosis in AML or MDS cells; and/or reduces colony formation of AML or MDS cells; and/or is effective to increase survival of the subject compared to untreated controls.

18. A method of inhibiting PAK1 in a subject, the method comprising administering to the subject a compound of Formula I, II, III or IV in an amount effective to inhibit PAK1 in a subject, wherein Formula I has the structure:

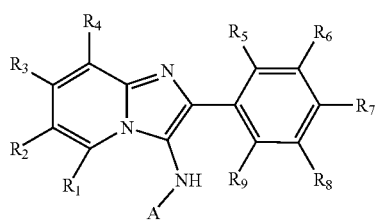

(I)

wherein $R_1$, $R_2$, $R_3$ and $R_4$ of Formula I are independently H, halogen, —OH, —NH$_2$, C1-C6 alkyl, —OCH$_3$, —COCH$_3$, 5- or 6-membered cyclic or heterocyclic, 5- or 6-membered aryl or heteroaryl, wherein the heteroaryl or heterocyclic contains one or more of the same or different heteroatom, or optionally substituted phenyl or benzyl, wherein the phenyl or benzyl is optionally substituted with one or more of halogen, —OH, —NH$_2$, —CH$_3$, or —OCH$_3$;

wherein $R_5$, $R_6$, $R_7$, $R_8$ and $R_9$ of Formula I are independently H, halogen, —OH, —NH$_2$, —NHCH$_3$, —N(CH$_3$)$_2$, C1-C6 alkyl, —OCH$_3$, —SH, —COCH$_3$, —SCH$_3$, 5- or 6-membered cyclic or heterocyclic, 5- or 6-membered aryl or heteroaryl, wherein the heteroaryl or heterocyclic contains one or more of the same or different heteroatom, or optionally substituted phenyl or benzyl, wherein the phenyl or benzyl is optionally substituted with one or more of halogen, —OH, —NH$_2$, —CH$_3$, or —OCH$_3$;

wherein A is a heteroaryl or heterocyclic containing one or more of the same or different heteroatom, or

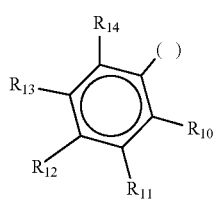

where ( ) represents the point of attachment to the molecular scaffold;

wherein $R_{10}$, $R_{11}$, $R_{12}$, $R_{13}$ and $R_{14}$ of Formula I are independently H, halogen, —OH, —NH$_2$, C1-C6 alkyl, —OCH$_3$, —COCH$_3$, and/or $R_{10}$ and $R_{11}$, or $R_{11}$ and $R_{12}$, or $R_{12}$ and $R_{13}$, or $R_{13}$ and $R_{14}$ of Formula I together form a 5- or 6-membered hetrocyclic or heteroaryl containing one or more of the same or different heteroatom;

or a pharmaceutically acceptable salt thereof;

wherein Formula II has the structure:

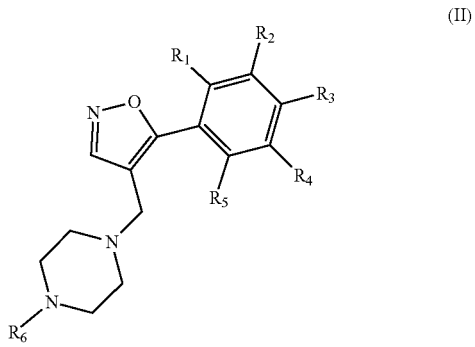

(II)

wherein $R_1$, $R_2$, $R_3$, $R_4$, $R_5$ and $R_6$ of Formula II are independently H, halogen, —OH, —NH$_2$, —NHCH$_3$, —N(CH$_3$)$_2$, C1-C6 alkyl, —OCH$_3$, —COCH$_3$ —SH, or —SCH$_3$, or a pharmaceutically acceptable salt thereof;

wherein Formula III has the structure:

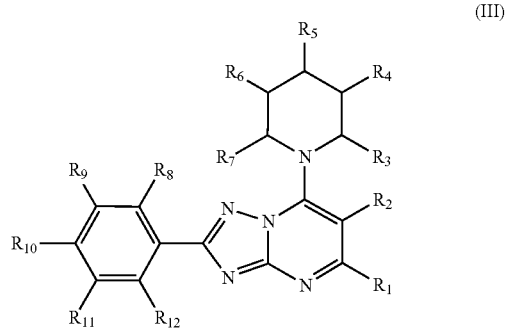

(III)

wherein $R_1$, $R_2$, $R_3$, $R_4$, $R_5$, $R_6$, $R_7$, $R_8$, $R_9$, $R_{10}$, $R_{11}$ and $R_{12}$ of Formula III are independently H, halogen, —OH, —NH$_2$, —NHCH$_3$, —N(CH$_3$)$_2$, C1-C6 alkyl, —OCH$_3$, —COCH$_3$, —SH, or —SCH$_3$, or a pharmaceutically acceptable salt thereof; and wherein Formula IV has the structure:

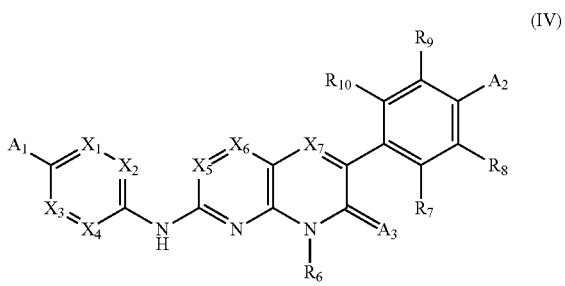

(IV)

wherein A1 and A2 of Formula IV are independently

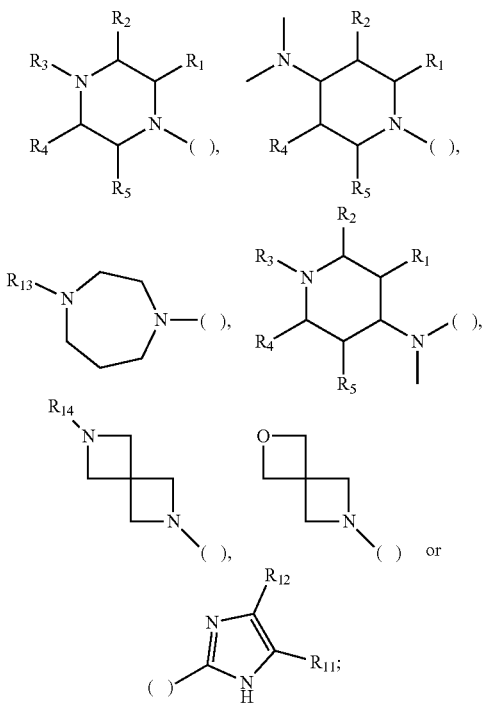

wherein $X_1$, $X_2$, $X_3$, $X_4$, $X_5$ and $X_7$ of Formula IV are independently CH or N;
wherein $X_6$ of Formula IV is CH, N or

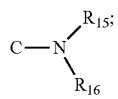

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$ and $R_{16}$ of Formula IV are independently H, halogen, —OH, —NH$_2$, —NHCH$_3$, —N(CH$_3$)$_2$, C1-C6 alkyl, —OCH$_3$, —COCH$_3$, —SH, or —SCH$_3$;
wherein A3 of Formula IV is O or N, and when A3 is N, $R_6$ is a C2 alkyl that bonds to the N of A3;
or a pharmaceutically acceptable salt thereof.

19. The method of claim 18, wherein the subject has elevated expression of PAK1 and/or increased PAK1 activity.

20. A compound having the structure

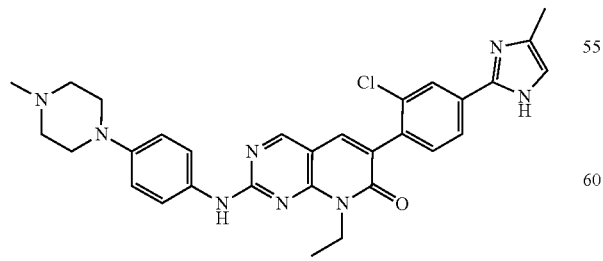

or a pharmaceutically acceptable salt thereof.

21. The method of claim 18, wherein one or both of $R_2$ and $R_6$ of Formula I is halogen.

22. The method of claim 18, wherein one or more of $R_1$, $R_4$, $R_{10}$ and $R_{14}$ of Formula I is —CH$_3$.

23. The method of claim 18, wherein $R_7$ of Formula I is —OH, —OCH$_3$, —N(CH$_3$)$_2$ or —SCH$_3$.

24. The method of claim 18, wherein $R_6$ or $R_7$ of Formula I is —OCH$_3$.

25. The method of claim 18, wherein A of Formula I is a pyridine, pyrimidine or pyrazine.

26. The method of claim 18, wherein the compound of Formula I has the formula

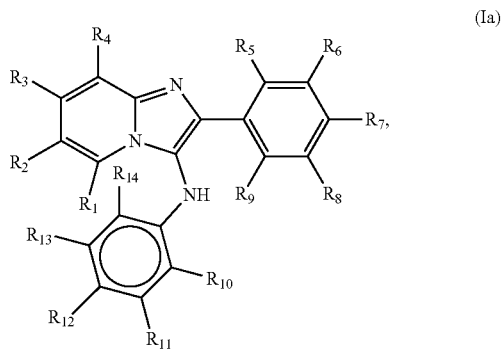

(Ia)

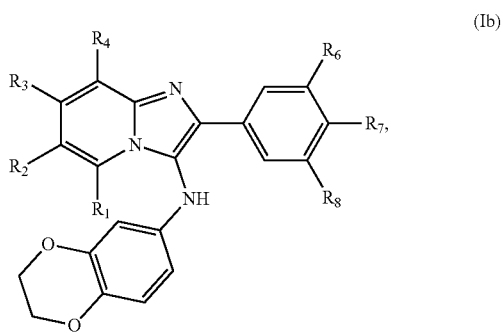

(Ib)

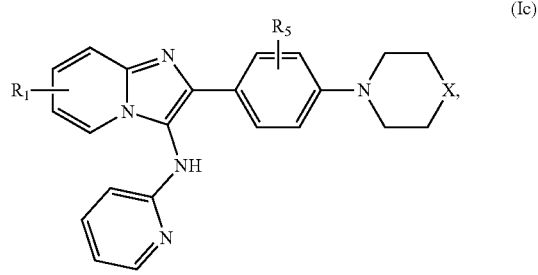

(Ic)

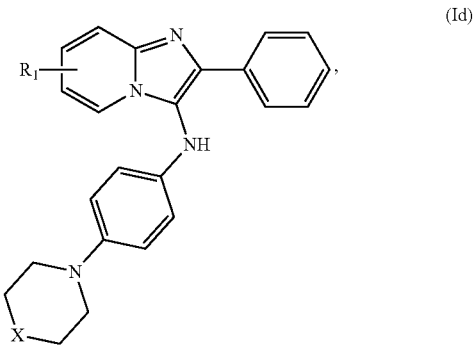

(Id)

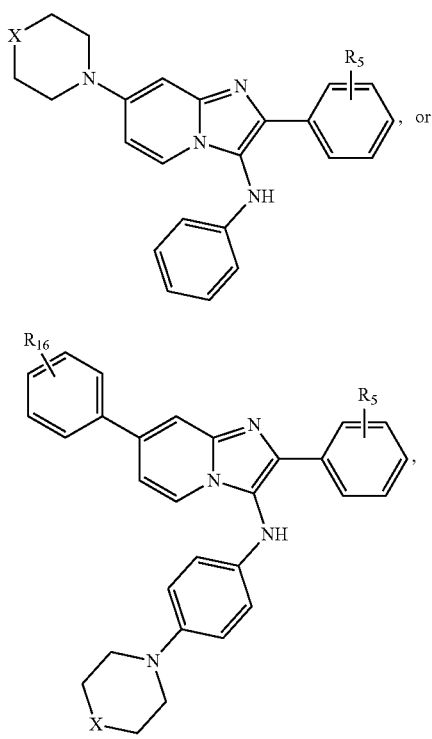

wherein $R_1$, $R_2$, $R_3$ and $R_4$ are independently H, halogen, —OH, —NH$_2$, —CH$_3$ or —OCH$_3$;

wherein $R_5$, $R_6$, $R_7$, $R_8$ and $R_9$ are independently H, halogen, —OH, —NH$_2$, —NHCH$_3$, —N(CH$_3$)$_2$, —CH$_3$, —OCH$_3$, —SH or —SCH$_3$, wherein $R_{10}$, $R_{11}$, $R_{12}$, $R_{13}$, $R_{14}$ and $R_{15}$ are independently H, halogen, —OH, —NH$_2$, —CH$_3$ or —OCH$_3$, wherein any X is independently CH$_2$, NH, O or S, or a pharmaceutically acceptable salt thereof.

27. The method of claim 18, wherein in the compound of Formula IV, $X_1$, $X_2$, $X_3$ and $X_4$ are CH; or $X_1$ is N, and $X_2$, $X_3$ and $X_4$ are CH; or $X_2$ is N, and $X_1$, $X_3$ and $X_4$ are CH; or $X_1$ and $X_3$ are N, and $X_2$ and $X_4$ are CH; or $X_5$ is N, and $X_6$ and $X_7$ are CH; or $X_5$ and $X_7$ are N, and $X_6$ is CH; or $X_6$ is N, and $X_5$ and $X_7$ are CH; or $X_5$ is N, $X_7$ is CH, and $X_6$ is

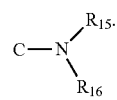

28. The method of claim 18, wherein the compound of Formula IV has the formula

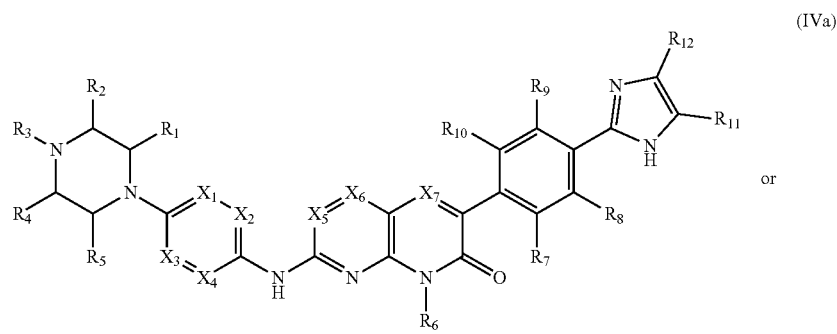

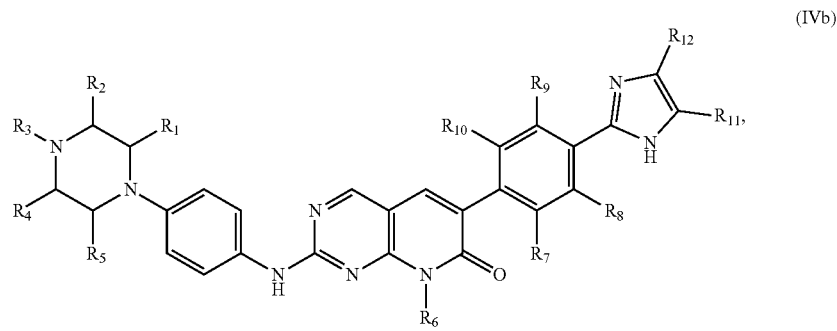

or a pharmaceutically acceptable salt thereof.

29. The method of claim 18, wherein any halogen is independently Br, Cl or I.

30. The method of claim 18, wherein any C1-C6 alkyl is independently —CH$_3$ or —CH$_2$CH$_3$.

31. The method of claim 18, wherein the compound of Formula I is selected from the group consisting of

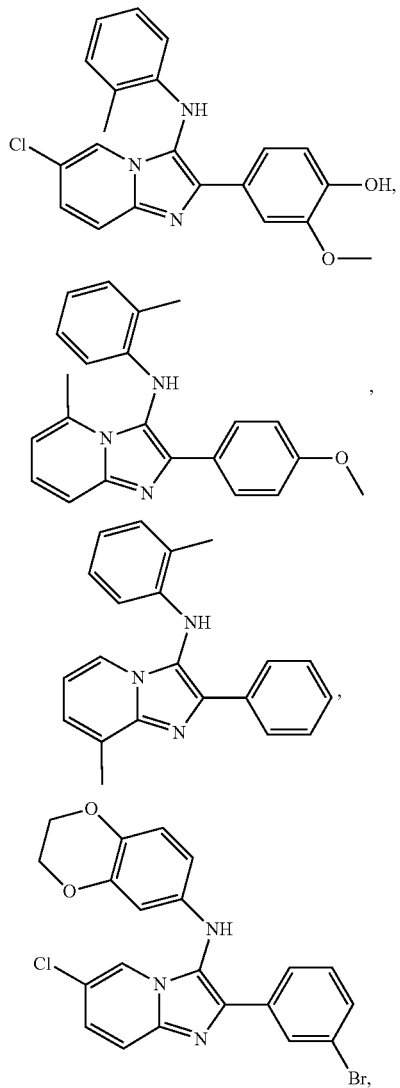

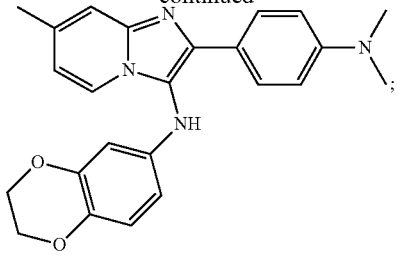

or a pharmaceutically acceptable salt thereof.

32. The method of claim 18, wherein the compound of Formula II has the structure

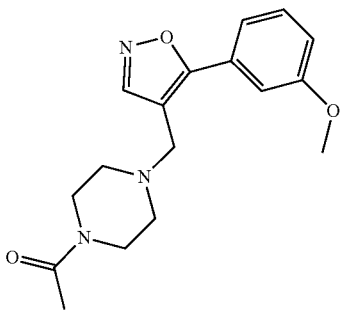 [SMILES: COc1cccc(-c2oncc2CN2CCN(C(C)=O)CC2)c1]

or a pharmaceutically acceptable salt thereof.

33. The method of claim 18, wherein the compound of Formula III has the structure

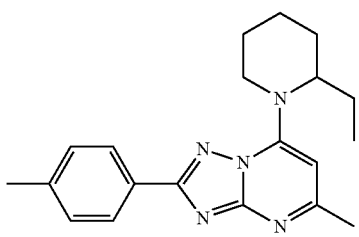 [SMILES: CCC1CCCCN1c1cc(C)nc2nc(-c3ccc(C)cc3)nn12]

or a pharmaceutically acceptable salt thereof.

34. The method of claim 18, wherein the compound of Formula IV has the structure

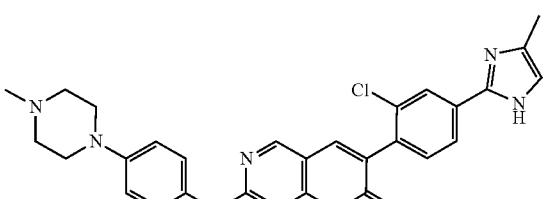

or a pharmaceutically acceptable salt thereof.

* * * * *